US007217570B2

(12) United States Patent
Herlyn et al.

(10) Patent No.: US 7,217,570 B2
(45) Date of Patent: May 15, 2007

(54) ORGANOTYPIC INTESTINAL CULTURE AND METHODS OF USE THEREOF

(75) Inventors: Meenhard Herlyn, Wynnewood, PA (US); Jiri Kalabis, Cambridge, MA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 406 days.

(21) Appl. No.: 10/485,283

(22) PCT Filed: Aug. 22, 2002

(86) PCT No.: PCT/US02/26663

§ 371 (c)(1),
(2), (4) Date: Jan. 29, 2004

(87) PCT Pub. No.: WO03/018752

PCT Pub. Date: Mar. 6, 2003

(65) Prior Publication Data
US 2004/0175367 A1    Sep. 9, 2004

Related U.S. Application Data

(60) Provisional application No. 60/314,111, filed on Aug. 23, 2001.

(51) Int. Cl.
*C12N 5/00* (2006.01)
*C12N 5/02* (2006.01)
*C12N 5/08* (2006.01)

(52) U.S. Cl. .................... 435/397; 435/371; 435/373; 435/384; 435/395

(58) Field of Classification Search ................ 435/371, 435/373, 384, 395, 397; 623/23.72, 23.75
See application file for complete search history.

(56) References Cited

U.S. PATENT DOCUMENTS

| 3,962,125 | A | 6/1976 | Armstrong |
| 5,073,492 | A | 12/1991 | Chen et al. |
| 5,194,596 | A | 3/1993 | Tischer et al. |
| 5,219,739 | A | 6/1993 | Tischer et al. |
| 5,480,975 | A | 1/1996 | Goldberg et al. |
| 5,661,132 | A | 8/1997 | Eriksson et al. |
| 5,731,190 | A | 3/1998 | Wickham et al. |
| 5,792,453 | A | 8/1998 | Hammond et al. |
| 5,869,037 | A | 2/1999 | Crystal et al. |
| 5,932,540 | A | 8/1999 | Hu et al. |
| 5,962,427 | A | 10/1999 | Goldstein et al. |
| 5,965,125 | A | 10/1999 | Mineau-Hanschke |
| 5,980,887 | A | 11/1999 | Isner et al. |
| 6,040,157 | A | 3/2000 | Hu et al. |
| 6,121,246 | A | 9/2000 | Isner |
| 6,187,767 | B1 | 2/2001 | Araneo et al. |
| 9,851,638 |   | 5/2001 | Herlyn |
| 6,486,133 | B1 | 11/2002 | Herlyn et al. |

| 6,521,225 | B1 | 2/2003 | Srivastava |
| 2004/0031067 | A1 | 2/2004 | Herlyn |

FOREIGN PATENT DOCUMENTS

| EP | 476983 A1 | 3/1992 |
| EP | 550296 A2 | 7/1993 |
| EP | 506477 B1 | 6/1999 |
| WO | WO-93/13807 A1 | 7/1993 |
| WO | WO-95/04142 A2 | 2/1995 |
| WO | WO-95/24473 A1 | 9/1995 |
| WO | WO-95/32708 A1 | 12/1995 |
| WO | WO-96/13597 | 5/1996 |
| WO | WO-96/23065 A2 | 8/1996 |
| WO | WO-96/26736 A1 | 9/1996 |
| WO | WO-96/26742 A1 | 9/1996 |
| WO | WO-96/27006 A2 | 9/1996 |
| WO | WO-96/39508 A1 | 12/1996 |
| WO | WO-96/39515 A1 | 12/1996 |
| WO | WO-97/12050 A1 | 4/1997 |
| WO | WO-97/13857 A1 | 4/1997 |
| WO | WO-97/38729 A1 | 10/1997 |
| WO | WO-98/19712 A1 | 5/1998 |
| WO | WO-98/39035 A1 | 9/1998 |
| WO | WO-98/39055 | 9/1998 |
| WO | WO-99/46364 A1 | 9/1999 |
| WO | WO-99/52356 A1 | 10/1999 |
| WO | WO-00/06195 A1 | 2/2000 |
| WO | WO-01/40455 | 6/2001 |
| WO | WO-02/30443 A2 | 4/2002 |
| WO | WO-03/018752 A2 | 3/2003 |

OTHER PUBLICATIONS

Day, R., 2006, Current Stem Cell Research & Therapy, vol. 1, No. 1, pp. 113-120.*
Baibakov et al., "Organotypic growth and differentiation of human mammary gland in sponge-gel matrix supported histoculture", *In Vitro Cell Dev. Biol. Anim.* Aug. 1994 30A(8):490-495.
Bekku et al., "Carbonic anhydrase I and II as a differentiation marker of human and rat colonic enterocytes", *Res. Exp. Med. (Berl)* Dec. 1998 198(4):175-185.

(Continued)

*Primary Examiner*—Shin-Lin Chen
(74) *Attorney, Agent, or Firm*—Howson & Howson LLP

(57) ABSTRACT

An organotypic culture comprises an artificial stroma overlayed with epithelial cells isolated from a human colon or intestine. The stroma comprises a mixture of collagen and human fibroblasts isolated from a human colon or intestine. The culture contains a factor that binds the IGF-1 receptor, a factor that binds the EGF receptor, and a factor that binds the LIF receptor. These factors may be added exogenously to the culture via medium or may be expressed by various recombinantly engineered cell types in the culture. The organotypic culture can result in growth that is in situ-like or emphasizes other physiological or morphological states, depending on the balance of factors in the growth media. The organotypic culture may be used in methods for screening of therapeutic, carcinogenic, or growth enhancement factors, or for treating intestinal injuries by applying to the site of an injury the intact culture or the components thereof.

19 Claims, 3 Drawing Sheets

OTHER PUBLICATIONS

Caesar et al., "A comparison of the specificity of phosphatidylcholine synthesis by human fetal lung maintained in either organ or organotypic culture", *J. Biochem.*Jul. 15, 1988 253(2):451-457.

Dahlqvist et al., "Development of the intestinal disaccharidase and alkaline phosphatase activities in the human fetus", *Clin. Sci.*Jun. 1966 30(3):517-528.

Evans et al., "Primary cultures for studies of cell regulation and physiology in intestinal eipthelium", *Ann. Rev. Physiol.*1994 56:399-417.

Fritsch et al., "Cytokines modulate fibroblast phenotype and epithelial-stroma interactions in rat intestine", *Gastroenterology* Mar. 1997 112(3):826-838.

Halttunen et al., "Fibroblasts and transforming growth factor beta induce organization and differentiation of T84 human epithelial cells", *Gastroenterology* Nov. 1996 111(5):1252-1262.

Ho S.B., "Cytoskeleton and other differentiation markers in the colon", *J. Cell. Biochem. Suppl.*1992 16G:119-128.

Karamuk et al., "Partially degradable film/fabric composites: textile scaffolds for liver cell culture", *Artif. Organs* Sep. 1999 23(9):881-884.

Kaye et al., "Colonic pericryptal fibroblast sheath: replication, migration, and cytodifferentiation of a mesenchymal cell system in adult tissue, II. Fine structural aspects of normal rabbit and human colon", *Gastroenterology* May 1968 54(5):852-865.

Kedinger et al., "Intestinal tissue and cell cultures", *Differentiation* 1987 36(1):71-85.

Kedinger et al., "Intestinal epithelial-mesenchymal cell interactions", *Ann. NY Acad. Sci.*Nov. 17, 1998, 859:1-17.

Menard et al., "Human intestinal brush border membrane hydrolases", in *Membrane Physiopathology* (G.B. ed.) Kluwer Academic Publishers, Oct. 1994 pp. 319-731.

Moyer M. P., "Tumor cell culture", *Methods Enzymol.*1995 524:153-165.

Oda et al., "Organotypic culture of human gallbladder epithelium", *Exp. Mol. Pathol.*Aug. 1995 63(1):16-22.

Oda et al., "Reconstituted human oral and esophageal mucosa in culture", *In Vitro Cell. Dev. Biol. Anim.*Jan. 1998 34(1):46-52.

Oda et al., "Culture of human main pancreatic duct epithelial cells", *In Vitro Cell. Dev. Biol. Anim.*Mar. 1998 34(3):211-216.

Pageot et al., "Human cell models to study small intestinal functions: recapitulation of the crypt-villus axis", *Microsc. Res. Tech.* May 15, 2000 49(4):394-406.

Parenteau et al., "Epidermis generated in vitro: practical considerations and applications", *J. Cell. Biochem.*Mar. 1991 45(3):245-251.

Pedersen et al., "A simple method to establish short-term cultures of normal human colonic epithelial cells from endoscopic biopsy specimens. Comparison of isolation methods, assessment of viability and metabolic activity", *Scand. J. Gastroenterol.*Jul. 2000 35(7):772-780.

Perreault et al., "Use of the dissociating enzyme thermolysin to generate viable human normal intestinal epithelial cell cultures", *Exp. Cell. Res.*May 1, 1996 224(2):354-364.

Perreault et al., "Primary cultures of fully differentiated and pure human intestinal epithelial cells", *Exp. Cell. Res.*Nov. 25, 1998 245(1):34-42.

Quaroni et al., "Establishment and characterization of intestinal epithelial cell cultures", *Methods Cell. Biol.*1980 21B:403-427.

Quaroni et al., "Cell dynamics and differentiation of conditionally immortalized human intestinal epithelial cells", *Gastroenterology* Oct. 1997 113(4):1198-1213.

Rogler et al. "Establishment of long-term primary cultures of human small and large intestinal epithelial cells", *Lab. Invest.*Jul. 1998 78(7):889-890.

Rousset M., "The human colon carcinoma cell lines HT-29 and Caco-2: two in vitro models for the study of intestinal differentiation", *Biochimie* Sep. 1986 68(9):1035-1040.

Schorkhuber et al., "Survival of normal colonic epithelial cells from both rats and humans is prolonged by coculcute with rat embryo colonic fibroblasts", *Cell. Biol. Toxical.*Jun. 1998 14(3):211-223.

Whitehead et al., "A method for the isolation and culture of human colonic crypts in collagen gels", *In Vitro Cell Dev. Biol.*Jun. 1987 23(6):436-442.

Whitehead et al., "Clonogenic growth of epithelial cells from normal colonic mucosa from both mice and humans", *Gastroenterology* Oct. 1999 117(4):858-865.

Lifebvre et al., "Developmental expression and cellular origin of the laminin aphla2, aplha4, and alpha5 chains in the intestine", *Dev. Biol.*Jun. 1, 1999 210(1):135-150.

Perreault et al., "Epithelial vs mesenchymal contribution to the extracellular matrix in the human intestine", *Biochem. Biophys. Res. Commun.*Jul. 9, 1998 248(1):121-126.

Sun et al., "Different HPV16 E6/E7 oncogene expression patterns in epithelia reconstructed from HPV16-immortalized human endocervical cells and genital keratinocytes", *Oncogene* Nov. 13, 1997 15(20):2399-2408.

Yan et al. "Human/Severe Combined Immunodeficient Mouse Chimeras, An Experimental in vivo Model System to Study the Regulation of Human Endothelial Cell-Leukocyte Adhesion Molecules", *J. Clin. Invest.*Mar. 1993 91(3): 986-96.

Sylvester et al., "Adenoviral-Mediated Gene Transfer in Wound Healing; Acute Inflammatory Response in Human Skin in the SCID Mouse Model", *Wound Repair Regen.*Jan.-Feb. 2000 8(1):36-44.

Oka et al., "Interleukin-8 Overexpression is Present in Pyoderma Gangrenosum Ulcers and Leads to Ulcer Formation in Human Skin Xeongrafts", *Lab. Invest.*Apr. 2000 80(4):595-604.

Juhasz et al., "Growth and Invasion of Human Melanomas in Human Skin Grafted to Immunodeficient Mice", *Am. J. Pathol* Aug. 1993 143(2):528-37.

Sauter et al., "Vascular Endothelial Growth Factor is a Marker of Tumor Invasion and Metastasis in Squamous Cell Carinomas of the Head and Neck", *Clin. Cancer Res.*Apr. 1999 5(4):775-782.

Setoguchi et al., "Ex. Vivo and In Vivo Gene Transfer to the Skin Using Replication-Deficient Recombinant Adenovirus Vectors", *J. Invest. Dermatol.*Apr. 1994 102(4):415-21.

Montesano et al., "Paracrine Induction of Angiogenesis In Vitro by Swiss 3T3 Fibroblasts", *J. Cell. Sci.*Oct. 1993 105:1013-1024.

Montesano et al., "Tumor-Promoting Phorbol Esters Induce Angiogenesis In Vitro", *Cell* Sep. 1985 42:469-477.

Montesano et al., "In Vitro Rapid Organization of Endothelial Cells into Capillary-Like Networks is Promoted by Collagen Matrices", *J. Cell. Biol.*Nov. 1983 97:1648-1652.

Kubota et al., "Role of Laminin and Basement Membrane in the Morphological Differentiation of Human Endothelial Cells in Capillary-Like Structures", *J. Cell. Biol.*Oct. 1988 107:1589-1598.

Ingber et al., "Mechanochemical Switching Between Growth and Differentiation During Fibroblast Growth Factor-Simulated Angiogensis In Vitro: Role of Extracellular Matrix", *J. Cell. Biol.* Jul. 1989 109:317-330.

Jackson et al., "Type I Collagen Fibrils Promote Rapid Vascular Tube Formation Upon Contact with the Apical Side of Cultured Endothelium", *Exp. Cell Res.*Jan. 1991 192:319-323.

Yang et al., "Functional Roles for PECAM-1 (CD31) and VE-Cadherin (CD144) in Tube Assembly and Lumen Formation in Three-Dimensional Collagen Gels", *Am. J. Pathol.*Sep. 1999 155:887-895.

Schechner et al., "In Vivo Formation of Complex Microvessels Lined by Human Endothelial Cells in an Immunodeficient Mouse", *Proc. Natl. Acad. Sci.*Aug. 1, 2000 97(16):9191-9196.

Hoying et al., "Angiogenic Potential of Microvessel Fragments Established in Three-Dimensional Collagen Gels", *In Vitro Cell Dev. Biol.*Jul.-Aug. 1996 32:409-419.

Hoying et al., "Effects of Basic Fibroblast Growth Factor on Human Microvessel Endothelial Cell Migration on Collagen I Correlates Inversely with Adhesion and is Cell Density Dependent", *J. Cell Physiol.*Aug. 1996 168:294-304.

Nicosia et al., "Growth of Microvessels in Serum-Free Matrix Culture of Rat Aorta. A Quantitative Assay of Angiogensis In Vitro", *Lab Invest.*Jul. 1990 63(1):115-122.

Black et al. "In Vitro Reconstruction of a Human Capillary-Like Network in a Tissue-Engineered Skin Equivalent", *FASEB J.*Oct. 1998 12(13):1331-40.

Foda et al., "Activation of Human Umbilical Vein Endothelial Cell Progelatinase A by Phorbol Myristate Acetate: a Protein Kinase C-Dependent Mechanism Involving a Membrane-Type Matrix Metalloproteinase", *Lab. Invest.*Feb. 1996 74(2):538-545.

Eming et al., "Enhanced Function of Culture Epithelium by Genetic Modification: Cell-Based Synthesis and delivery of Growth Factors" *Biotechnol. Bioeng.*Oct. 5, 1996 52(1): 15-23.

Carmeliet et al., "Molecular Analysis of Blood Vessel Formation and Disease", *Am. J. Phys.*Nov. 1997 273(5PT2):H2091-H2104.

Sers et al., "MUC18, A Melanoma-Progression Associated Molecule, and its Potential Role in Tumor Vascularization and Hematogenous Spread", *Cancer Res.*Nov. 1, 1994 54(21):5689-5694.

Swiercz et al., "Angiostatic Activity of Synthetic Inhibitors of Urokinase Type Plasminogen Activator", *Oncology Reports* May 1999 6(3):523-526.

Pelletier et al., "An In Vitro Model for the Study of Human Bone Marrow Angiogenesis: Role of Hematopoietic Cytokines", *Lab. Invest.*Apr. 2000 80(4):501-511.

Cooper et al., "Use of a Composite Skin Graft Composed of Culture Human Keratinocytes and Fibroblasts and a Collagen GAG Matrix to Cover Full-Thickness Wounds on Athymic Mice", *Surgery* Feb. 1991 109(2):198-207.

Less et al., "A Freeze-Injured Skin Graft Model for the Quantitative Study of Basic Fibroblast Growth Factor and Other Promoters of Angiogenesis in Wound Healing", *Brit. J. of Plastic Surg.*Jul. 1994 47:349-359.

Sakamoto et al., "Vessel Formation by Chorodial Endothelial Cells In Vitro Is Modulated by Retinal Pigment Epithelial Cells", *Arch. Ophthalmol.*Apr. 1995 113(4):512-520.

Thompson et al., "Site-Directed Neovessel Formation In-Vivo", *Science* Sep. 9, 1988 241(4871)1349-1352.

Hansson et al., "Transient Expression of Insulin-Like Growth Factor I Immunoreactivity by Vascular Cells During Angiogenesis", *Exp. Mol. Pathol.*Feb. 1989 50(1):125-138.

Takeshita et al., "Gene Transfer of Naked DNA Encoding for Three Isoforms of Vascular Endothelial Growth Factor Stimulates Collateral Development In Vivo", *Lab. Invest.*Oct. 1996 75(4):487-501.

Harris et al., "Gene Therapy Through Signal Transduction Pathways and Angiogenic Growth Factors as Therapeutic Targets in Breast Cancer", *Cancer* Aug. 1, 1994 74(3 Suppl):1021-1025.

Mühlhauser et al., "$VEGF_{165}$ Expressed by a Replication-Deficient Recombinant Adenovirus Vector Induces Angiogenesis in Vivo", *Circulation Res.*Dec. 1995 77(6):1077-1086.

Peault et al., "Gene Transfer to Human Fetal Pulmonary Tissue Developed in Immunodeficient SCID Mice", *Hum. Gene Ther.*Sep. 1994 5(9):1131-1137.

Allen-Hoffman et al., "Fibronectin Levels Are Enhanced in Human Fibroblasts Overexpressing the c-sis Protooncogene", *J. Biol. Chem.*Mar. 25, 1990 265(9):5219-5225.

Bywater et al., "Expression of Recombinant Platelet Derived Growth Factor A—and B-chain Homodimers in Rat-1 Cells and Human Fibroblasts Reveals Differences in Protein Processing and Autocrine Effects", *Mol. Cell. Biol.*Jul. 1988 8(7):2753-2762.

Soballe et al., "Carcinogenesis in Human Skin Grafted to SCID Mice", *Cancer Res.*Feb. 15, 1996 56(4):757-764.

Meier, "Human Melanoma Progression in Skin Reconstructs", *Am. J. Pathol.*Jan. 2000 156(1):193-200.

Berking et al. "Human Skin Reconstruct Models: A New Application for Studies of Melanocyte and Melanoma Biology" *Histol. Histopathol.*Apr. 2001 16(2):669-674.

Miller et al., "Targeted Vectors for Gene Therapy", *FASEB* Feb. 1995 9:190-199.

Deonarain, "Ligand-Targeted Receptor-Mediated Vectors for Gene Delivery", *Exp. Opin. Ther. Patents* 1998 8(1):53-69.

Verma et al., "Gene Therapy—Promises, Problems, and Prospects", *Nature* Sep. 18, 1997 389:239-242.

Parker et al., "Transplantation of Discordant Xenografts: A Challenge Revisited", *Xenotransplantation* aug. 1996 17(8):373-378.

Minanov et al., "Recent Advances and the Potential for Clinical Use of Xenotransplantation", *Curr. Opin. Cardiology* Mar. 1996 11:214-220.

"Skeletal Tissues" in *Wheater's Functional Histology*, $4^{rd}$ Ed., (Wheater et al., Eds.) 1993 Churchill Livingston, New York: 170-173.

Riddell et al., "T-Cell Mediated Rejection of Gene-Modified HIV-Specific Cytotoxic T Lymphocytes in HIV-Infected Patients", *Nat. Med.*Feb. 1996 2(2):216-223.

Velazquez et al., "The Vascular Phenotype of Melanoma Metastasis", *Clin. Exp. Metastasis* 2003 20(3):229-235.

Eming et al., "Genetically Modified Human Epidermis Overexpressing PDGF-A Directs the Development of a Cellular and Vascular Connective Tissue Stroma when Transplanted to Athymic Mice—Implications for the Use of Genetically Modified Keratinocytes to Modulate Dermal Regeneration", *J. Invest. Dermatol.*Dec. 1995 105(6):756-763.

Magovern et al., "Direct In Vivo Gene Transfer to Canine Myocardium Using a Replication-Deficient Adenovirus Vector", *Ann. Thorac. Surf.*Aug. 1996 62(2):425-434.

Thomas, Taber's Cylopedic Medical Dictionary, Ed. 17 1993 pp. 1808-1811.

Magovern et al., "Regional Angiogenesis Induced in Nonischemic Tissue by an Adenoviral Vector Expressing Vascular Endothelial Growth Factor", *Human Gene Therapy* Jan. 20, 1997 8:215-227.

Chen et al., "High-Efficiency Transformation of Mammalian Cells by Plasmid DNA", *Mol. Cell. Biol.*Aug. 1987 7(8);2745-2752.

Greenhalgh et al., "PDGF and FGF Stimulate Wound Healing in the Genetically Diabetic Mouse", *Am. J. Pathology* Jun. 1990 136(6):1235-1246.

Mustoe et al., "A Phase II Study to Evaluate Recombinant Platelet-Derived Growth Factor-BB in the Treatment of Stage 3 and 4 Pressure Ulcers", *Arch. Surg.* Feb. 1994 129:213-219.

Hübner et al., "Differential Regulation of Pro-Inflammatory Cytokines During Wound Healing in Normal and Glucocorticoid-Treated Mice", *Cytokine* Jul. 1996 8(7):548-556.

Andree et al., "In Vivo Transfer and Expression of a Human Epidermal Growth Factor Gene Accelerates Wound Repair", *Proc. Natl. Acad. Sci. USA* Dec. 1994 91:12188-12192.

Kreuger et al., "Genetically Modified Skin to Treat Disease: Potential and Limitations", *J. Invest. Dermatol.*1994 103:76S-84S.

Hengge et al., "Cytokine Gene Expression in Epidermis with Biological Effects Following Injection of Naked DNA", *Nature Genetics* Jun. 1995 1-:161-166.

Benn et al., "Particle-Mediated Gene Transfer with Transforming Growth Factor-β1 cDNAs Enhances Wound Repair in Rat Skin", *J. Clin. Invest.*Dec. 1996 98(12):2894-2902.

Grinnell, "Wound Repair, Keratinocyte Activation and Integrin Modulation", *J. Cell. Sci.*Jan. 1992 101:1-5.

Falanga et al., "Workshop on the Pathogenesis of Chronic Wounds", *M. Invest. Dermatol.*Jan. 1994 102:125-127.

Ciernik et al., "Puncture-Mediated Gene Transfer to the Skin", *Human Gene Therapy* May 20, 1996 7:893-899.

Pierce et al., "Detection of Platelet-Derived Growth Factor (PDGF)-AA in Actively Healing Human Wounds Treated with Recombinant PDGF-BB and Absence of PDGF in Chronic Nonhealing Wounds", *J. Clin. Invest.*Sep. 1995 96:1336-1350.

Ono et al., "Studies on Cytokines Related to Wound Healing in Donor Site Wound Fluid", *J. Dermatol. Sci.*Nov. 1995 10:241-245.

Lynch et al., "Role of Platelet-Derived Growth Factor in Wound Healing: Synergistic Effects with Other Growth Factors", *Proc. Natl. Acad. Sci. USA* Nov. 1987 84:7696-7700.

Pierce et al., "Platelet-Derived Growth Factor (BB Homodimer), Transforming Growth Factor-β1 and Basic Fibroblast Growth Factor in Dermal Wound Healing", *Am. J. Pathol.*Jun. 1992 140(6):1375-1388.

Steed et al., "Randomized Prospective Double-Blind Trial in Healing Chronic Diabetic Foot Ulcers", *Diabetes Care* Nov. 1992 15(11):1598-1604.

Robson et al., "Recombinant Human Platelet-Derived Growth Factor-BB for the Treatment of Chronic Pressure Ulcers", *Ann. Plast. Surg.*Sep. 1992 29:193-201.

Pierce et al., "Role of Platelet-Derived Growth Factor in Wound Healing", *J. Cell. Biochem.*Apr. 1991 45:319-326.

Ziegelstein et al., "Initial Contact and Subsequent Adhesion of Human Neutrophils or Monocytes to Human Aortic Endothelial Cells Releases in Endothelial Intracellular Calcium Store", *Circulation* Oct. 1994 90(4):1899-1907.

Alberts et al., *Molecular Biology of the Cell*, 3rd Ed. 1994 Garland Publishing, New York, NY:1140.

Carmeliet et al., "Adenovirus-Mediated Transfer of Tissue-Type Plasminogen Activator Augments Thrombolysis in Tissue-Type Plasminogen Activator-Deficient and Plasminogen Activator Inhibitor-1-Overexpressing Mice", *Blood* Aug. 15, 1997 90(4):1527-1534.

Carmeliet et al., "Inhibitory Role of Plasminogen Activator Inhibitor-1 in Arterial Wound Healing and Neointima Formation", *Circulation* Nov. 4, 1997 96(9):3180.

Hsu et al. "Cadherin Repertoire Determines Partner-Specific Gap Junctional Communication during Melanoma Progression", *J. Cell. Sci.* May 6, 2000 113:1535-1542.

Leconte et al., "Adenoviral-Mediated Expression of Antisense RNA to Fibroblast Growth Factors Disrupts Murine Vascular Development", *Developmental Dynamics* Dec. 1998 213:421-430.

Lee et al., "Phenotype, Function, and In Vivo Migration and Survival of Allogeneic Dendritic Cell Progenitors Genetically Engineered to Express TGF-$\beta^{1,2}$", *Transplantation* Dec. 27, 1998 66(12):1810-1817.

Liechty et al., "Adenoviral-Mediated Overexpression of Platelet-Derived Growth Factor B Corrects Ischemic Impaired Wound Healing", *Soc. Invest. Dermatol.* Sep. 1999 113(3):375-383.

Meschia, "Management of Acute Ischemic Stroke, What is the Role of tPA and Antithrombotic Agents?", *Postgraduate Medicine* May 15, 2000 107(6):85.

Nagai et al., "Role of Plasminogen System Components in Focal Cerebral Ischemic Infarction: A Gene Targeting and Gene Transfer Study in Mice", *Circulation* May 11, 1999 99(18):2440.

Hsu et al., "Adenoviral Gene Transfer of $\beta$3 Integrin Subunit Induces Conversion from Radial to Vertical Growth Phase in Primary Human Melanoma", *Am. J. Pathology* Nov. 1998 153(5):1435-1442.

Mohan et al., "Adenovirus-Mediated Delivery of Antisense Gene to Urokinase-Type Plasminogen Activator Receptor Suppresses Glioma Invasion and Tumor Growth", *Cancer Research* Jul. 15, 1999 59:3369-3373.

Sauter et al., "Antisense Cyclin D1 Induces Apoptosis and Tumor Shrinkage in Human Squamous Carcinomas", *Cancer Res.* Oct. 1, 1999 59:4876-4881.

Montesano et al. "Basic Fibroblast Growth Factor Induces Angiogenesis In Vitro", *Proc. Natl. Acad. Sci. USA* Oct. 1986 83:7297-7301.

Gerritsen et al, "Wound Healing Around Bone-Anchored Percutaneous Devices in Experimental Diabetes Mellitus," *Biomed Mater Res.* 2000 53(6):702-9.

Bonifati et al., "Serum Endothelin-1 Levels Are Increased in Psoriatic Patients and Correlate with Disease Severity", *Int. J. Immunopathol. and Pharmacol.* 1997 10(1):81-82.

Atillasoy et al., "UVB Induces Atypical Melanocytic Lesions and Melanoma in Human Skin", *Am. J. Pathol.* May 1998 152(5):1179.

Baker et al., "Development of Recombinant Adenoviruses that Drive High Level Expression of the Human Metalloproteinase-9 and Tissue Inhibitor of Metalloproteinase-1 and -2 Genes: Characterization of Their Infection into Rabbit Smooth Muscle Cells and Human MCF-7 Adenocarcinoma Cells", *Matrix Biol.* Dec. 1996 15:383.

Baltzer et al., "Genetic Enhancement of Fracture Repair: Healing of an Experimental Segmental Defect by Adenoviral Transfer of the BMP-2 Gene", *Gene Therapy* May 2000 7:734-739.

Blagosklonny et al., "In Vitro Evaluation of a p53-Expressing Adenovirus as an Anti-Cancer Drug", *Int. J. Cancer* Jul. 29, 1996 67:386-392.

Vlodavsky et al., "Involvement of Heparan Sulfate and Related Molecules in Sequestration and Growth Promoting Activity of Fibroblast Growth Factors", *Cancer and Metastasis Reviews* Jun. 1996 15(2):177-186.

Thurston et al., "Angiopoietin-1 Protects the Adult Vasculature Against Plasma Leakage", *Nature Med.* Apr. 2000 6(4):460.

Tumova et al., "Heparan Sulfate Proteoglycans on the Cell Surface: Versatile Coordinators of Cellular Functions", *Int. J. Biochem. & Cell. Biol.* Mar. 2000 32:269-288.

Prabhu et al., "Suppression of Cancer Cell Growth by Adenovirus Expressing $p^{21\ WAF1/CIP1}$ Deficient in PCNA Interation", *Clin. Cancer Res.* Jul. 1996 2:1221-1229.

Martin et al., "Adenovirus-Mediated Expression of Green Fluorescent Protein", *Gene Therapy* May 1997 4:493-495.

Fenjves et al., "Approaches to Gene Transfer Keratinocytes", *J. Invest. Dermatol.* Nov. 1994 103(5) Supplement: 714.

Graham et al., "A New Technique for the Assay of Infectivity of Human Adenovirus 5 DNA", *Virology* Apr. 1973 52:456-467.

Harvey et al., "Cellular Immune Responses of Healthy Individuals to Intradermal Administration of an E1 E3 Adenovirus Gene Transfer Vector", *Human Gene Therapy* Nov. 20, 1999 10:2823-2837.

Hurber et al., "Efficient In Vitro Transfection of Human Keratinocytes with an Adenovirus-Enhanced Receptor-Mediated System", *Soc. Invest. Dermatol.* Apr. 4, 2000 114(4):661.

Lee et al., "Antitumor Effects of an Adenovirus Expressing Antisense Insulin-Like Growth Factor I Receptor on Human Lung Cancer Cell Lines", *Cancer Res.* Jul. 1, 1996 56:3038-3041.

Lu et al., "A Model For Keratinocyte Gene Therapy: Preclinical and Therapeutic Considerations", *Proc. Assoc. Am. Physicians* Mar. 1996 108(2):165.

Lu et al., "Topical Application of Viral Vectors for Epidermal Gene Transfer", *Soc. Invest. Dermatol.* May 1997 108(5):803.

Veelken et al., "Primary Fibroblasts from Human Adults as Target Cells for Ex Vivo Transfection and Gene Therapy", *Human Gene Therapy* Oct. 1994 5:1203-1210.

Satyamoorthy et al., "An Antisense Strategy for Inhibition of Human Melanoma Growth Targets the Growth Factor Pleiotrophin", *Pigment Cell Res.* 2000 13(Suppl. 8):87-93.

Morris et al., "Clinical Protocol: A Phase I Study of Intralesional Administration of an Adenovirus Vector Expressing the HSV-1 Thymidine Kinase Gene (AdV.RSV-TK) in Combination with Escalating Doses of Ganciclovir in Patients with Cutaneous Metastatic Malignant Melanoma", *Human Gene Therapy* Feb. 10, 2000 11:487-503.

Nesbit et al., "$\alpha$5 and $\alpha$2 Integrin Gene Transfers Mimic the PDGF-B-Induced Transformed Phenotype of Fibroblasts in Human Skin", *Lab. Invest.* Sep. 2001 81(9):1263-1274.

Oshawa et al., "Enhancement of Adenovirus-Mediated Gene Transfer into Dermal Fibroblasts In vitro and In vivo by Polythylene Glycol 6000", *J. Dermatol.* Apr. 2000 27:244-251.

Miki et al., "An Artificial Esophagus Constructed of Cultured Human Esophageal Epithelial Cells, Fibroblasts, Polyglycolic Acid Mesh, and Collagen", *ASAIO Journal*, 45(5): 502-508 (1999).

* cited by examiner

ORGANOTYPIC INTESTINAL CULTURE AND METHODS OF USE THEREOF

CROSS-REFERENCE TO RELATED APPLICATIONS

This application is a national stage of PCT/US02/26663, filed Aug. 22, 2002, which claims the benefit of the priority of US Provisional Patent Application No. 60/314,111, filed Aug. 23, 2001.

Aspects of this invention were supported by the National Institutes of Health grant Nos. CA74294, PK50306, and CAI 08185. The United States government may have certain rights in this invention.

BACKGROUND OF THE INVENTION

The normal human colonic epithelium undergoes continuous cycle of renewal with a dynamic equilibrium between proliferation, differentiation and apoptosis. Within the base of each crypt (i.e., a deep indentation formed by involutions of the colonic epithelium), yet to be identified stem cells give rise to progenitor cells that divide rapidly four to six times before differentiation. In the mouse intestine, up to 60% of the approximately 250 epithelial cells in a single crypt divide twice daily, yielding up to 260 new cells. Thus, the intestinal epithelium harbors one of the most rapidly dividing cell types in any mammalian organ. Polarized cells migrate along the crypt's basement membrane towards the apical surface of colonic villi, where the cells undergo differentiation as indicated by shifts in cytoskeletal markers such as cytokeratins, cytoplasmic carbonic anhydrase isozyme II, and the brush border enzyme alkaline phosphatase.

Induction of differentiation is incompletely understood, but appears to result from a concerted interplay between growth factors produced by epithelial and stromal cells and signals from basement membrane components. The basement membrane is synthesized by both epithelial and mesenchymal cells, and it contains numerous fenestrations through which processes of myofibroblasts and/or epithelial cells extend. Little is known about the role of fibroblasts in modulating proliferation and differentiation of colonic epithelial cells except that fibroblasts can prolong their survival. Heterologous cross-talk between epithelial and mesenchyrnal compartments involves basement membrane molecules and paracrine factors. The mesenchymal cells apparently produce as yet undefined growth factors for the epithelial cells.

Normal human colonic epithelial cells have been difficult to maintain in vitro. Thus knowledge about intestinal cell regulation has been derived from studies with cell cultures isolated from experimental animals and human colon cancer-derived cell lines. Normal epithelial cells survive only a few days in culture, which has limited studies of proliferation and differentiation. For example, in Whitehead et al's culture (Whitehead R. H. et al, 1999 *Gastroenterology*, 117:858–865), normal adult colonic crypt cells were embedded into an acellular collagen gel matrix over a feeder layer of bovine aortic endothelial cells, and grown as isolated islands of cells, which increased their survival for up to 16 days.

Normal human cells grown as isolated cultures in monolayer lose many characteristics of those in situ and often resemble the phenotype of cancer cells. For example, colonic cells immortalized with viral oncogenes lose their typical epithelial morphology and neither polarize nor differentiate, limiting the use of their usefulness for biological studies.

In contrast, cells in a tissue-like context maintain a similar phenotype as those growing in situ. Organotypic reconstructs and cultures can serve as replacement organs, as models for the study of the basic biology of organs, and as screening systems for development of drugs, to identify drug candidates as well as to observe candidate drug activity, such as its transport into organs, or dosage requirements. Obviously, the most useful organotypic cell reconstructs and cultures have a long shelf life and allow the component cells to maintain their normal cellular activities and morphologies and the ability to function within the organ.

Organotypic culture models for esophagus, bladder, pancreatic duct, breast, lung, liver, and human skin have all been used for studies of tissue physiology, drug delivery and transformation. The cells in those organotypic cultures retain many of the functions they had in situ. For example, normal human melanocytes in the epidermis of an organotypic skin culture were shown to develop close adhesive and gap junctional communications with basal layer keratinocytes.

In contrast to cells of most other organs, normal human colon cells have been difficult to maintain in vitro. Currently available normal human intestinal epithelial cells are derived from the small intestine and exhibit undifferentiated features, while differentiated enterocytes remain in culture for only 10–12 days. Models of human intestine in culture are not suitable for studies of proliferation and differentiation. The cultured cells survive for only a few days. Co-culture of intestinal epithelial cells with fibroblasts or myofibroblasts could prolong survival. To improve survival, immortalization of colonic cells with genes from oncogenic viruses has been attempted. However, the transformed cells lost their typical epithelial morphology and did not polarize or differentiate.

There remains a need in the art for compositions and methods that provide a useful source of normal human intestinal epithelial cells which maintains in situ-like properties for use in studies of colon biology, screening for drug absorption and efficacy and for therapeutic uses, such as in transplantation or the treatment of colon lesions.

SUMMARY OF THE INVENTION

In one aspect, this invention provides an organotypic culture comprising an artificial stroma comprising a mixture of collagen and human fibroblasts isolated from a human colon or intestine, the stroma overlayed with epithelial cells isolated from a human colon or intestine. Present in the culture are at least one growth factor that binds the insulin growth factor-1 (IGF-1) receptor, at least one growth factor that binds the epidermal growth factor (EGF) receptor, and at least one growth factor that binds the leukemia inhibitory factor (LIF) receptor. Desirably this organotypic culture resembles the in situ colon or small intestine tissue. In another embodiment, cells of the organotypic culture are in specific pre-hemostatic stages.

In another aspect, the invention provides a culture medium suitable for growth of an organotypic culture of claim 1 comprising a base media, at least one of insulin or IGF-1, at least one of EGF-1 or tumor growth factor (TGF)-alpha, and LIF. In another embodiment, the medium includes a base media, 1% fetal calf serum (FCS) and/or transferrin, and at least one factor selected from among insulin or IGF-1, EGF or TGF-alpha, endothelin-3 (ET-3), hepatocyte growth factor (HGF), LIF, stem cell factor (SCF), and autocrine mobility factor (AMF). Still additional embodiments are disclosed below.

In still another aspect, the invention provides a method of preparing an organotypic culture as above-described. This method involves assembling an artificial stroma by mixing collagen and fibroblasts; and seeding the artificial stroma with epithelial cells in the presence of at least one growth factor that binds the IGF-1 receptor, at least one growth factor that binds the EGF receptor, and at least one growth factor that binds the LIF receptor.

In yet another aspect, the invention provides a method of in vitro screening of an agent comprising contacting an above-described organotypic culture with a selected agent in a vessel, and observing the effect of the agent upon the culture. Depending upon the desired effect sought, this method enables one to select from among many agents, an agent suitable as e.g., a drug candidate, or an agent that affects cell replication, proliferation or differentiation in a desirable way. This screening method permits the identification of agents that would affect wound repair, agents that are carcinogens, and/or agents that absorb or cross membrane transport into tissue.

In still a further aspect, the invention provides a method for screening an agent for repairing effect on intestinal epithelial cell injury. This method involves disrupting the layer of epithelial cells on an above-described organotypic culture; and contacting the site of disruption with the selected agent; The effects of the agent on the repair of the epithelial cell layer are observed, thereby enabling selection of an agent which promotes repair of the epithelial cell layer and/or is capable of repairing the injury.

In yet another aspect, the invention involves a method for enhancing epithelial cell repair at an in vivo site of intestinal or colonic injury. This method involves delivering to the site of the injury at least one of collagen, fibroblasts, a growth factor that binds the IGF-1 receptor, a growth factor that binds the EGF receptor, and a growth factor that binds the LIF receptor, or a combination of these factors. In one embodiment, the fibroblasts may be recombinantly engineered to express one or more of the other factors.

In still another aspect, the invention involves a method of treating an intestinal wound by placing an organotypic culture as defined herein on an intestinal wound in a patient.

Other aspects and advantages of the present invention are described further in the following detailed description of the embodiments thereof.

DETAILED DESCRIPTION OF THE INVENTION

Figure 1:
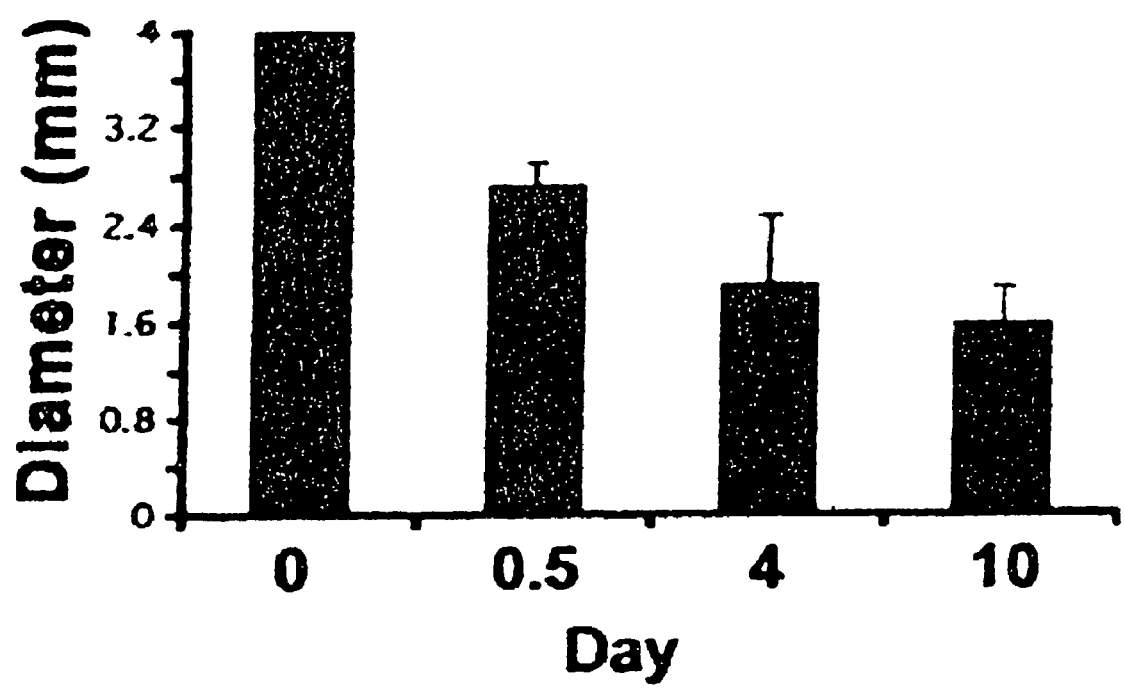
FIG. 1 is a graph plotting diameter (mm) of constriction of collagen over time of incubation (mean±SD of 8 samples) in a colonic culture preparation including fetal colon (18 weeks' gestation) after isolation of mucosa and after the epithelial layer is stripped, including the bottom of crypts.

This invention provides a novel organotypic culture model, also referred to as an intestinal reconstruct, that mimics in situ conditions of the normal human colon. This culture is thus useful in the investigation of colon epithelial cell proliferation and differentiation, and permits the dissection of the role of individual growth factors in the cross-talk between the epithelial and mesenchyrnal compartments that form the normal intestinal wall. Thus this organotypic culture is useful for screening of agents which may have therapeutic or toxic effects on the intestinal wall, as well as other research and therapeutic uses described below.

I. The Organotypic Culture of the Invention

In the normal intestine, both epithelial cells and myofibroblasts contribute to formation of the basement membrane (Kedinger, M. et al, 1998. *Ann. N.Y. Acad. Sci.* 859: 1–17). The organotypic culture of this invention comprises an artificial stroma (also known as a stromal reconstruct or stromal matrix) overlayed or seeded with epithelial cells isolated from a human colon or human intestine. This culture further contains at least one growth factor that binds the insulin growth factor-1 (IGF-1) receptor, at least one growth factor that binds the epidermal growth factor (EGF) receptor, and at least one growth factor that binds the leukemia inhibitory factor (LIF) receptor. A reconstruct comprising either type of epithelial cells is referred herein as an intestinal reconstruct. This combination of all three components, i.e. stromal cells, collagen, and colonic or small intestine epithelial cells grown in contact with the collagen and stromal cells is important in allowing the growth of the epithelial cells and assembly of an in situ like reconstruct. The reconstruct can be grown in a media which comprises base media supplied with specific subsets of factors, which allows for identification of agents that effect specific morphological and interactive phenomena of cells within the reconstruct.

A. The Artificial Stroma

The artificial stroma is a matrix formed by a mixture of collagen and human fibroblasts isolated from a human colon or intestine. Optionally, the stromal reconstruct further comprises smooth muscle cells. Still optionally, the stromal reconstruct may contain other types of cells, such as neurons, perycites, endothelial cells and macrophages, among others. The artificial stroma provides a collagen substrate with stromal cells to closely mimic physiological conditions. Thus, in the three-dimensional organotypic culture, the artificial stroma permits the isolated human fetal colonic epithelial cells to be maintained in their native milieu. The fibroblasts constrict the collagen in the artificial stroma, allowing the colonic epithelial cells to migrate, proliferate and differentiate.

Collagen from any source can be used in the artificial stroma. In one embodiment collagen type I is used in the stroma; in another embodiment collagen type III is used in the stroma. Collagen types I and III are the major types of collagen present in the normal stroma and intestine. In one embodiment, the collagen used in the artificial stroma is human collagen. In another embodiment, another mammalian collagen may be used to form the artificial stroma, such as bovine tendon acid-extracted collagen (Organogenesis, Canton, Mass.). Another commercially available collagen which can be used in this invention is rat tail collagen (Collaborative Research Products).

Any human fibroblasts are useful in admixture with the collagen to form the artificial stroma. In one embodiment, the fibroblasts are human colonic fibroblasts. In a specific embodiment, the fibroblasts are adult human colon fibroblasts. In another embodiment the fibroblasts are fetal human colon fibroblasts. In another embodiment the fibroblasts are adult human small intestinal fibroblasts. In still another embodiment, the fibroblasts are fetal human small intestinal fibroblasts. Still another source of fibroblasts are human fibroblast stem cells, which may be derived from bone marrow. The fibroblasts can be newly isolated from the above sources or the fibroblast cells can be from an established cell line.

Methods of establishing and propagation of mammalian fibroblast cell lines are well known in the art (Bell et al., 1993 *J. Invest Dermat.*, 81 *Suppl.:* 2s–10s). A few such cell lines were produced from fetus explants as described in the Examples. One such line used as a source for fibroblasts for the artificial stroma of this invention is FFC331. It was propagated on Dulbecco's modified minimum essential medium (DMEM, GIBCO BRL, Rockviile, Md.) supplemented with 10% fetal calf serum (FCS, Cansera, Rexdale, Ontario, Canada) and antibiotics. Cultures were used up to passage 10. Use of cells from cell lines that did not undergo excessive passages is preferred. Other sources of suitable cell lines may be obtained from commercial or institutional laboratories and facilities, such as the American Type Cell Culture, Manassass, Va.

In one embodiment of the artificial stroma, human smooth muscle cells are also embedded in the collagen, along with the fibroblasts. Human smooth muscle cells from any organ or tissue can be used, for example, from the abdomen or the vascular system. However, vascular smooth muscle cells are preferred. The cells can be freshly isolated from adult humans, from fetal cell sources, or as stem cells from the bone marrow. Alternatively, the cells can be obtained from an established cell line. One such line predominantly used as a source of smooth muscle cells was HIAS119 (Dr. E. Levine, The Wistar Institute). The HIAS119 cells were isolated from human large vessels and maintained in medium M199, supplemented with 10% FCS, 2 mM L-glutamine, and 50 g/ml of bovine hypothalamic extract (Sorger, T. et al., 1995 *In Vitro Cell Dev. Biol. Anim.,* 31:671–683). Other sources of suitable cell lines may be obtained from commercial or institutional laboratories and facilities, such as the American Type Cell Culture, Manassass, Va.

The ratio of fibroblast and smooth muscle cells (if used) is subject to a large degree of variability. Preferably, the ratio of fibroblast:smooth muscle cells is about 1:1 or higher. In a particularly preferred embodiment, the ratio is 10:1 fibroblasts:smooth muscle cells.

In another embodiment, the fibroblasts and optionally the smooth muscle cells for admixture into the collagen matrix to form the artificial stroma are genetically engineered to permit the cells to overexpress one or more factors that are desirable for growth and maintenance of the organotypic culture of this invention. The techniques, vectors and factors useful for the generation of such fibroblasts (and optionally smooth muscle cells) are described in detail below, under the heading "Manipulation of Cells of the Organotypic Culture".

For preparation of the artificial stroma, the collagen is suspended in suitable medium. In one embodiment, used in the Examples below, the medium is DMEM supplemented with Vitamin C (Sigma) at 50 M/liter, L-glutamine (GIBCO; BRL) at 1.66 mM and 1% fetal calf serum (FCS) to a final concentration of 0.9 to 1.1 mg/ml. The suspension is neutralized, preferably to about pH 7.0. In one embodiment, a pH of 7.2 is used. Before the collagen gel hardens (usually within about 15 minutes), fibroblasts and optional smooth muscle cells are added. The stromal (i.e., fibroblast) cells are added to collagen in a small volume of a buffer. Any conventional buffer is useful, including e.g., DMEM. The buffer may be selected from a variety of buffers known to those of skill in the art to be used in the compositions of the invention and include, without limitation, phosphate buffered saline (PBS) or isotonic saline, such as ISOTON®II diluent, U.S. Pat. No. 3,962,125, [Beckman Coulter, Inc., Miami, Fla.], Tris buffer, the organic buffer N-(2-Acetamido)-2-iminodiacetic acid (ADA), or Pyrophosphate buffer or combinations thereof. Also useful are acetate buffers, succinate buffers, maleate buffers, citrate buffers, imidazole buffers, carbonate buffers, MES buffer, MOPS buffer, and HEPES buffer, among many that may be readily selected by one of skill in the art. Still other buffers such as the Good buffers identified in Good, N. E. et al. 1966 *Biochemistry* 5, 467 and Good, N. E., and Izawa, S. 1972 *Methods Enzymol.* 24, 53 may be utilized depending upon the functional requirements of the formulation as determined by one skilled in the art.

Depending upon whether the cells embedded in the collagen have been manipulated to overexpress desired factors, the artificial stromal reconstruct is thereafter maintained in medium which may be complete media, a minimal (or base) media, or base media supplemented with certain essential and optional growth factors, as desired as discussed below.

In yet another embodiment, the artificial stroma is overlaid or coated with an extracellular matrix or matrix protein prior. In one embodiment, the fibroblast and/or smooth muscle cell-embedded collagen is treated with the matrix protein Laminin-2 $\alpha 2\beta 1\gamma 1$. In another embodiment the fibroblast and/or smooth muscle cell-embedded collagen is treated with the matrix protein Laminin-1 $\alpha 2\beta 1\gamma 1$. In yet another embodiment, the fibroblast and/or smooth muscle cell-embedded collagen is treated with a combination of such matrix proteins. One commercially available combination is Matrigel® gel matrix (Collaborative Research, Bedford, Mass.), which contains Laminin-1 and other matrix proteins, such as collagen IV and nitrogen. Preferably, the fibroblast and/or smooth muscle cell-embedded collagen is treated with the matrix protein prior to seeding the epithelial cells.

Laminin-1 induces the polarization (differentiation) of carcinoma derived cells and normal cells. Laminin-2 increases the proliferation rate of epithelial cells in the organotypic culture. Generally, the fibroblast-embedded collagen is treated by addition of about 20 μg/ml of laminin to the growth media in which the artificial stroma is maintained. The artificial stroma is maintained in the laminin-enriched media for about an hour, washed with base media, and placed in complete media or base media enriched in factors in accordance with the invention, with or without added laminin. If laminin is added, it is added to about 10 μg/ml.

Matrix proteins, such as Laminin, from any source can be used to coat the fibroblast-embedded collagen. Several commercially available matrix proteins include, without limitation, laminin 2 α2β1γ1 (human Laminin, Life Technologies, Rockville, Md.), laminin 1- α2β1γ1 (Sigma), mouse laminin 1 (Life Technologies), and Matrigel® matrix (Collaborative Research, Bedford, Mass.) (Burgeson, R E. et al., 1994 *Matrix Biol.*, 14:209–211 and Page, K C. et al., 1990 *Biol. Reprod.*, 43:659–664).

B. The Epithelial Cells

In the organotypic culture of this invention, epithelial cells are overlaid or seeded on the surface of the artificial stroma. In one embodiment, human intestinal cells are used. In another embodiment human colonic or large intestinal epithelial cells are used. In another embodiment, human small intestinal epithelial cells are used. In one embodiment the epithelial cells are adult human colon epithelial cells. In one embodiment, the epithelial cells are fetal human colon epithelial cells. In another embodiment, the epithelial cells are adult human small intestinal epithelial cells. In another embodiment, the epithelial cells are fetal human small intestinal epithelial cells. In still another embodiment, the epithelial cells are human epithelial stem cells. Such stem cells may be obtained from human bone marrow. Such stem cells may be embryonic stem cells.

The epithelial cells can be newly isolated from the above sources. A method of isolation of such cells is described in the Examples. See also Rogler et al. 1998 *Lab. Invest.* 78: 889–900. Known alternative and modified methods extant in the art can be used to isolate the human colonic or small intestine epithelial cells. Alternatively, the epithelial cells can be derived from an established epithelial cell line, such as an adenoma or carcinoma cell line. Suitable cell lines may be obtained from commercial or institutional laboratories and facilities, such as the American Type Cell Culture, Manassass, Va.

In another embodiment, the epithelial cells for overlaying or seeding the artificial stroma to form the organotypic culture of this invention are genetically engineered to permit the cells to overexpress one or more factors that are desirable for growth and maintenance of the culture. The techniques, vectors and factors useful for the generation of such genetically engineered epithelial cells are described in detail below, under the heading "Manipulation of Cells of the Organotypic Culture".

C. Optional Endothelial Cell Layer

In yet another embodiment, a layer of endothelial cells in a suitable medium may be provided to underlie the artificial stroma and permit the organotypic culture to become vascularized. These endothelial cells form a capillary network induced by the fibroblasts in the artificial stroma and infiltrate the collagen/fibroblast stroma to form microvessels. Such a system is analogous to that described for a vascularized skin reconstruct in PCT Patent Publication No. WO02/30443, published on Apr. 18, 2002 and incorporated by reference herein.

In one embodiment, human endothelial cells are used. In another embodiment, the endothelial cells are adult human endothelial cells. In another embodiment, the endothelial cells are fetal human endothelial cells. In still another embodiment, the endothelial cells are human endothelial stem cells. Such stem cells may be obtained from human bone marrow. Such stem cells may be embryonic stem cells.

The endothelial cells can be newly isolated from the above sources. Known methods extant in the art can be used to isolate the human colonic or small intestine endothelial cells. Alternatively, the endothelial cells can be derived from an established endothelial cell line. Suitable cell lines may be obtained from commercial or institutional laboratories and facilities, such as the American Type Cell Culture, Manassass, Va.

In another embodiment, the endothelial cells for underlaying the artificial stroma to form a vascularized organotypic culture of this invention are genetically engineered to permit the cells to overexpress one or more factors that are desirable for growth and maintenance of the culture. The techniques, vectors and factors useful for the generation of such genetically engineered epithelial cells are described in detail below, under the heading "Manipulation of Cells of the Organotypic Culture".

D. Manipulation of Cells of the Organotypic Culture

In certain embodiments of the present invention, the fibroblast or optional smooth muscle cells present in the artificial stroma, the epithelial cells overlaying the stroma, and the optional endothelial cells may be engineered to express or overexpress a desirable factor or protein to provide the organotypic culture with nutrients suitable for growth, proliferation, differentiation, and long-term survival. Included among these proteins are one or more of the factors which are otherwise added to the base media or growth media, as discussed below to assemble various embodiments of the organotypic intestinal culture of this invention.

In one embodiment of the organotypic culture, at least a portion of the fibroblasts used for admixture with collagen to fomn the artificial stroma are infected or transfected, prior to admixture with the collagen, with a recombinant vector comprising a DNA sequence encoding a selected growth factor, under the control of regulatory sequences capable of expressing that factor in the fibroblast. In one embodiment the selected growth factor is a growth factor that binds the IGF-1 receptor, such as insulin or IGF-1. In another embodiment the growth factor is one that binds the EGF receptor, such as EGF or TGF-alpha. In still another embodiment the growth factor is one that binds the LIF receptor, such as LIF. In still another embodiment, the growth factor binds the hepatocyte growth factor (HGF) receptor, such as HGF. TGF-β3 is a factor that could be expressed to supply a factor alternative to HGF. In still another embodiment the growth factor is a growth factor that binds the stem cell factor (SCF) receptor, e.g., SCF. In yet another embodiment, the factor is a growth factor that binds the endothelin-3 (ET-3) receptor, such as ET-3. In another embodiment, the fibroblast is engineered to overexpress a growth factor that binds the platelet derived growth factor (PDGF) receptor, e.g. PDGF. In still another embodiment, the fibroblast is engineered to express a matrix protein, such as Laminin-1 or Laminin-2.

In an alternative or additional embodiment of an organotypic culture of this invention, at least a portion of the epithelial cells used for seeding the artificial stroma are infected or transfected before seeding with a recombinant vector comprising a DNA sequence encoding a selected growth factor, under the control of regulatory sequences capable of expressing said factor in the epithelial cell. In one such embodiment, the epithelial cell expresses a growth factor that binds the IGF-1 receptor. In another embodiment, the epithelial cell overexpresses a growth factor that binds the EGF receptor. In still another embodiment, the epithelial cell overexpresses a growth factor that binds the SCF receptor. In yet another embodiment, the epithelial cell overexpresses a growth factor that binds the autocrine motility factor (AMF) receptor. In still another embodiment, the epithelial cells overexpress a growth factor that binds the endothelin receptor A or the endothelin receptor B.

In still alternative embodiments in which smooth muscle cells are also embedded in the artificial stroma, the smooth muscle cells may also be engineered to express one or more desired growth factors or matrix proteins, including any one of the growth factors or proteins previously identified above. In another embodiment of the organotypic culture, in which a layer of endothelial cells are employed to underlie the fibroblast-embedded artificial stroma, at least a portion of such endothelial cells are infected with a recombinant vector comprising a DNA sequence encoding a selected growth factor or matrix protein, under the control of regulatory sequences capable of expressing said factor protein in the endothelial cells. One of skill in the art may select a suitable growth factor or protein for expression, if desired.

The components for the transfection or infection of one or more of the above cell types in the culture are readily available in the art. For example, polynucleotide sequences encoding the proteins and growth factors identified above, and plasmid and vector constructs containing these sequences for expression in mammalian cells are known. For example, these sequences are available from GenBank or readily accessible scientific publications, or even commercially available. See, for example, LIF mRNA sequence (GenBank Accession No. XM009915); ET-3 mRNA sequence (GeneBank Accession No. XM009583); and TGFβ-3 mRNA sequence (GeneBank Accession No. J0324), and associated publications, thereof. One of skill in the art, e.g., in molecular biology, can readily isolate, obtain, and manipulate these and other such sequences for expression, preferably regulated (inducible) expression of those genes.

For example, these sequences of the desired growth factors or proteins, useful fragments thereof, and modifications thereto may be constructed recombinantly using conventional molecular biology techniques, site-directed mutagenesis, genetic engineering or PCR, and the like by utilizing the information provided herein. For example, methods for producing the above-identified modifications of the sequences, include mutagenesis of certain nucleotides and/or insertion or deletion of nucleotides, or codons, thereby effecting the polypeptide sequence by insertion or deletion of, e.g., non-natural amino acids, are known and may be selected by one of skill in the art. See, e.g., Sambrook et al., *Molecular Cloning. A Laboratory Manual.*, 2d Edit., Cold Spring Harbor Laboratory, New York (1989); Ausubel et al. (1997), Current Protocols in Molecular Biology, John Wiley & Sons, New York).

Briefly described, a recombinant molecule or vector is constructed in which the polynucleotide sequence encoding the selected protein is operably linked to a heterologous expression control sequence permitting expression of the protein in the desired mammalian cells. Numerous types of appropriate expression vectors and vector components suitable for use in this invention are known in the art.

Exemplary vectors and vector components, including selected constitutive and inducible promoters, are readily available from a variety of academic and commercial sources, and include, e.g., adeno-associated virus (International patent application No. PCT/US91/03440), adenovirus vectors (M. Kay et al, 1994 *Proc. Natl. Acad. Sci. USA,* 91:2353 (1994); S. Ishibashi et al, 1993 *Clin. Invest.,* 92:883 (1993)), or other viral vectors, e.g., various poxviruses, vaccinia, etc. In one embodiment of this invention, the desired vectors for use in infecting the cells of the organotypic culture are recombinant adenovirus vectors, including such vectors deficient in the E1 gene and partially defective in the E3 gene, such as those described in International Patent Publication No. WO 98/39055, published Sep. 11, 1998 and incorporated herein by reference. Other known adenovirus vectors of the art may be similarly useful.

Exemplary regulatory sequences, including suitable promoters, may be selected for high level constitutive expression of the selected factor or protein in the cell of the organotypic culture of this invention, including, without limitation, the cytomegalovirus (CMV) promoter, the SV40 promoter, the dihydrofolate reductase promoter, the β-actin promoter. Inducible promoters, regulated by exogenously supplied compounds, are also useful and include, without limitation, the zinc-inducible sheep metallothionine (MT) promoter, the dexamethasone (Dex)-inducible mouse mammary tumor virus (MMTV) promoter, the T7 polymerase promoter system; the tetracycline-repressible or tet-inducible systems. Other types of inducible promoters which may be useful in this context are those which are regulated by a specific physiological state, e.g., temperature, acute phase, a particular differentiation state of the cell, or in replicating cells only. The native promoter for the growth factor may be used and is when expression of the transgene must be regulated temporally or developmentally, or in a tissue-specific manner. Tissue-specific promoters may also be used in these vectors. Other native expression control elements, such as enhancer elements, polyadenylation sites or Kozak consensus sequences may also be used to mimic the native expression.

Thereafter, methods for ex vivo transduction, infection, or transfection of such vectors in the cells of the present invention also are well known. See, e.g., Nesbit et al., 1999 *Oncogene* 18: 6469–76; Phaneuf et al. 2000 *Mol. Med.,* 6: 96–103; and Satayamoorthy et al. 1997 *Cancer Res.,* 57: 873–6 (1997); International Patent Publication No. WO 01/40455, published Jun. 7, 2001; International Patent Publication No. WO96/13597, published May 9, 1996, among others and the references cited above.

The preparation or synthesis of the polynucleotide sequences and recombinant vectors disclosed herein, as well as the components and techniques useful for preparing same are well within the ability of the person having ordinary skill in the art using available material. The particular selection of the vector, vector components, assembly methods and transfection/infection methods used to generate the recombinant cells useful in this embodiment of the present invention are not a limitation of this invention. One of skill in the art may make a selection among these methods and components without departing from the scope of this invention and using the guidance provided by this application.

E. Medium and Growth Factors

As discussed above, various media may be employed in the production of the components of the organotypic culture and to achieve the desired proliferation, differentiation and survival of the culture.

For use in maintaining the artificial stroma prior to addition of the epithelial cells, a base media containing only the minimum nutrients is useful. A suitable base medium can include MCDB 201 medium (Difco), L15 medium (Sigma), DMEM with 10% fetal calf serum (FCS), among others. Other base media are known in the art. Optionally, such base media can include transferrin and serum components, such as FCS or antibiotics. One specific embodiment of a base medium useful for maintaining the artificial stroma contains 4 parts MCDB 201 medium, 1 part L15 medium (Sigma), 5

μg/ml transferrin (Sigma), and the antibiotics, streptomycin and gentomycin, 50 μg/ml, each.

In embodiments of this invention in which the cells in the organotypic culture are not engineered to overexpress certain growth factors, or only engineered to express one or less than all of the necessary factors, the medium used in the organotypic culture can supply the factors exogenously. Along with the release of fibroblast-derived growth factors, colonic epithelial cells in the organotypic culture require exogenous growth factors in culture medium for survival, especially during the first 3 days of culture. During this time, the collagen-constricting fibroblasts have not yet reached a homeostatic balance. Besides growth, migration of the colonic cells appears to be critical for homeostasis of the colonic epithelium. Such growth factors are commercially available from a variety of sources, identified in the Examples below.

A minimally supporting base medium for maintaining the organotypic culture of this invention further includes a growth factor that binds to the epidermal growth factor (EGF) receptor, a growth factor that binds to the insulin-like growth factor-1 (IGF-1) receptor, and a growth factor that binds to the leukemia inhibitory factor (LIF) receptor. Growth factors that bind the IGF-1 receptor include insulin and IGF-1 and are survival factors. Growth factors that bind the EGF receptor include EGF and tumor growth factor-alpha (TGF-alpha). EGF can stimulate intestinal epithelial cells in vivo and enhance colonogenic growth in vivo (Chailler, P. and Menard, D., 1999 *Front. Biosci.,* 4:D87–101). Among growth factors that bind the LIF receptor is LIF. LIF was the most significant factor for proliferation of eukaryocytes while inhibiting differentiation. This factor can be secreted by colorectal carcinoma cells to stimulate their proliferation (Kamohara, H. et al 1994 *Res Commun Mol Pathol Pharmacol* 85, 131–140) by colorectal carcinoma cells to stimulate their proliferation (Guimbaud, R. et al, 1998 *Eur Cytokine Netw* 9, 607–612; and Bellone, G. et al, 1997 *Cell. Physiol.,* 172, 1–11) by binding to its receptor expressed by colonic epithelial cells (Rockman, S. P et al, 2001 *J. Gastroenterol. Hepatol.* 16, 991–1000) by binding to its receptor expressed by colonic epithelial cells (Rockman, S. P. et al, 2001 *J. Gastroenterol Hepatol* 16, 991–1000). LIF activity was dependent on collagen-embedded fibroblasts. In the presence of the essential growth and survival factors insulin and epidermal growth factor (EGF), leukemia inhibitory factor (LIF) had the most profound effect on stimulation of proliferation of the epithelial cells in the organotypic culture, while preventing differentiation, indicating that LIF is critical for maintaining the phenotype of colonic crypt cells.

In contrast to the minimally supporting medium for the organotypic culture, a complete growth medium generally consists of the base medium supplemented with a variety of growth factors in addition to those identified in the minimally supporting medium. In complete growth medium, the growth factors induce a balance between proliferation and differentiation. Among such additional growth factors includes, without limitation, a protein that binds the human basic fibroblast growth factor (bFGF) receptor, a protein that binds the endothelin-3 (ET-3) receptor, a protein that binds the endothelin receptor A or B, a protein that binds the hepatocyte growth factor (HGF) receptor, a protein that binds the stem cell factor (SCF) receptor, a protein that binds the autocrine motility factor (AMF) receptor, and a protein that binds the platelet derived growth factor (PDGF) receptor. Optionally, such media can include transferrin and serum components, such as fetal calf serum (FCS). See, e.g., the medium described in Nesbit M., et al. 1999 *Oncogene* 18:6469–6476.

For example, one embodiment of a suitable growth media for the organotypic cultures includes EGF, LIF and insulin, and at least one of SCF and ET-3. As demonstrated in the Examples, LIF was synergistically active with SCF and ET-3, which show little activity on their own. LIF also synergizes with HGF, which on its own induces a flat, migratory epithelial phenotype (Nusrat A. et al., 1994 *Clin. Invest.* 93: 2056–2065). LIF may also have an effect on goblet cells which form in the organotypic construct of this invention. Goblet cells are terminally differentiated due to their high levels of mucin production. As shown in the examples below, the inventors observed that 33% of goblet cells in the organotypic culture incorporated BrdU during a 10-day culture period, suggesting that they developed through differentiation of proliferating enterocytes. LIF does not induce differentiation of cells to the neuroendocrine phenotype, which steadily declined in the culture, suggesting that other factors are needed for this cell type. LIF was critical for proliferation of enterocytes and inhibited expression of the differentiation marker carbonic anhydrase II. In the presence of LIF, the number of goblet cells remained stable, whereas enteroendocrine cell number declined. LIF stimulation of cultures remained dependent on the presence of fibroblasts in the matrix. In the absence of other growth factors, LIF induced formation of disorganized structures of stratified and semi-stratified cells, suggesting that the homeostatic balance in the normal human colon requires cooperation with differentiation-inducing factors.

In still another medium used in the examples, a complete growth medium contained a base media and insulin, transferrin, EGF, ET-3, HGF, LIF, SCF, AMF, and FCS, which combined to stimulate growth, migration and differentiation of the colonic cells. Only cultures in HGF-containing medium were able to cover the entire collagen matrix, consistent with evidence that this growth factor provides migratory stimulation. Although EGF can also stimulate migration, it alone was not sufficient to initiate it in the organotypic reconstruct of the invention.

In combination with other factors in the medium, LIF was one of the most important mitogens and morphogens. In the presence of LIF and EGF only, colonic cells formed a polarized monolayer of highly cylindrical cells. Proliferation and cell-type specific morphology were further enhanced and altered, respectively, by the combination of SCF, ET-3, EGF, and insulin. Under these conditions, epithelia formed highly disorganized structures of stratified and pseudostratified cells. Goblet cells lost polarity and deposited mucus towards the basement membrane. The number of goblet cells decreased in LIF-containing media, most likely because LIF can inhibit differentiation. Dysplastic morphology and decreased number of goblet cells are early indications of premalignancy in the human colon (Wargovich, M J. et al. 1983 *J. Natl. Cancer Inst.,* 71:125–131 and Archer, M C. et al. 1992 *Environ. Health Perspect.,* 98:195–197). In complete medium, other not yet identified growth factors must have induced a balance between proliferation and differentiation.

Still other specific media for use in maintaining the organotypic cultures of this invention are described with specificity in the Examples below.

II. Methods for Preparing an Organotypic Culture of this Invention

In general, the method of preparing an organotypic culture of the invention comprises the primary steps of assembling the artificial stroma by mixing collagen and fibroblasts as described in detail above and thereafter, seeding the artificial stroma with epithelial cells in the presence of a growth factor that binds the IGF-1 receptor, a growth factor that binds the EGF receptor, and a growth factor that binds the LIF receptor. As described above the growth factors may be provided exogenously by the media or may be provided by the use of recombinantly engineered fibroblasts or epithelial cells that express one or more of these factors.

However, more complex organotypic cultures of the invention may be prepared by layering the artificial stroma over an endothelial cell layer, as described above. Additionally or alternatively, a matrix protein, e.g., laminin may be used to coated the artificial stroma prior to the seeding of the epithelial cells. Still other embodiments are provided by the use of smooth muscle cells or neural cell types added to the artificial stroma. Still a further embodiment of an organotypic culture of this invention is provided by seeding a malignant cell on the surface of the artificial stroma, such as a epithelial cancer cell. By such addition of a cancer cell type on the surface of the artificial stroma, the organotypic culture can become a model of tumor formation or tumor-stroma interaction. Examples of readily available malignant cell types are a tumor from a human patient, or established tumors in an animal, or established malignant cell lines. In lieu of malignant cell seeding, a whole tumor could be implanted in a reconstruct. See, e.g., Ochalek and Kleist, 1993 *Clin. Lab. Anal.*, 7: 155–163.

In one embodiment for preparation of an organotypic culture of this invention, colonic epithelial cells or small intestine epithelial cells in media are seeded or overlaid on the surface of the artificial stroma. In one embodiment of the method of generating the culture, the media volume is reduced from the time of overlaying and for about 1 to about 1.5 hours, to allow the epithelial cells to attach to the artificial stroma. The seeding can occur at anytime after the artificial stroma is established. The seeding preferably occurs within 24 hours after the artificial stroma is assembled.

The resulting organotypic reconstruct is grown on a minimally supporting medium, i.e., base media plus LIF, IGF-1 or insulin, and EGF or TGF-alpha, or various formulations of complete media, including the base medium plus optionally any other factor(s) from among the growth factors identified above, transferrin or 1–2% FCS. The growth conditions (e.g., temperature, oxygenation, resemble standard mammalian cell growth conditions. For example, the culture is incubated at 37° C. in 5% $CO_2$ in growth media which was changed daily for 7 days, then changed three times/week for the next 21 days.

The fibroblasts and optionally smooth muscle cells act to constrict the stromal reconstruct and allow epithelial cells to expand and cover the organotypic culture. The close proximity of the fibroblasts to epithelial cells in the organotypic culture allows formation of a microenvironment that closely mimics mucosal compartments in vivo. This microenvironment includes the formation of the three types of cells that normally populate the intestinal epithelial wall, e.g., goblet cells, enteroendocrine cells and enterocytes. The inventors have maintained the epithelial cells and normal colonic homeostasis of cell growth and differentiation in the organotypic culture containing fibroblast-embedded artificial stroma in a complex growth factor-supplemented medium for more than 1 month, and up to 40% of the entire cell population had proliferated during a 10-day incubation period.

Goblet cells proliferated or differentiated from proliferating enterocytes, whereas enteroendocrine cells were only maintained without proliferation. Cooperative effects of growth factors were dependent on the presence of fibroblasts. The migratory properties of colonic epithelia in the organotypic culture of this invention resembled intestinal wound healing with epithelial restitution (Dignass, A. U., 2001 *Inflamm. Bowel Dis.*, 7:68–77).

As described in the Examples below, in one embodiment of an organotypic culture of this invention, human fetal colonic epithelial cells were isolated and seeded on a collagen type I matrix embedded with colonic fibroblasts. The epithelial cells rapidly spread from clusters and proliferated, and within 3 days, a columnar layer of polarized epithelium surrounded the surface of the constricted collagen matrix. The polarized enterocytes developed brush borders, tight junctions and desmosomes, and goblet and enteroendocrine cells were dispersed throughout the epithelium. A balance of growth and differentiation was maintained for several weeks in the presence of collagen-embedded fibroblasts and a complex mixture of growth factors.

In another embodiment, the artificial stroma containing fibroblasts and smooth muscle cells constricted the collagen down to about 10% of its original volume, allowing the epithelial cells to migrate and proliferate around the entire collagen matrix, producing an organotypic culture of this invention.

As described in the Examples below, several embodiments of the organotypic cultures of this invention were grown either in a complete media, i.e. the base media supplemented with insulin, transferrin, EGF, ET-3, HGF, LIF, SCF, AMF, and only 1% FCS, which combined to stimulate growth, migration and differentiation of the cells, or in a base media supplemented with 1% FCS, insulin, and EGF (the minimal media) and subsets of the other factors, which identified some of the factors to be crucial for specific phenomena, i.e. cell migration, survival, proliferation and differentiation. In other embodiments, prior to the seeding of epithelial cells, the stromal reconstruct is incubated in the media further including laminin-1 and/or laminin-2, as described above.

This organotypic culture of normal human colon cells provides evidence that microenvironmental factors regulate the proliferation and differentiation of these cells. Both the presence of stromal cells and growth factor supplementation in the medium were critical. When the intestinal organotypic reconstruct was grown in the complete media, the epithelium quickly covered all free surfaces and maintained a polarized monolayer with a balance of proliferation and apoptosis. There was differentiation into all major epithelial cell types, including enterocytes, goblet cells, and neurosecretory cells. In the intestinal reconstruct of the present invention, the mesenchymal (stromal) cells were observed to actively migrated and accumulated beneath the epithelium and aligned with the epithelium cells. This is likely due to attractants released by the colonic cells or to the trapping of randomly migrating fibroblasts at the epithelial interface and the developing basement membrane. During contraction of the collagen gel, the majority of the mesenchymal cells expressed α-smooth muscle actin (α-SMA), indicating differentiation to myofibroblasts., as also observed in fibroblasts exposed to TGF-β (Berking, C., et al, 2001 *Cancer Res.*, 61:8306–8316). Myofibroblasts, i.e., mature and differentiated fibroblasts, and mature smooth muscle cells are known to produce and excrete growth factors including HGF, bFGF, IGF, and KGF (Nusrat A. et al., 1994 *J. Clin. Invest.* 93: 2056–2065 and Powell, D. W., et al, 1999 *Am. J. Physiol.*, 277:C1–9). Fibroblasts directly subjacent to the epithelium continued to express A-SMA for prolonged periods, as is seen in situ, suggesting that epithelial-derived signals induce a myofibroblast phenotype (Sappino, A P. et al., 1989 *Virchows Arch. A. Pathol. Anat. Histopathol.* 415:551–557). The contribution of mesenchymal cells to epithelial cell growth and differentiation is thus two-fold: 1) production of soluble growth factors; and 2) production of matrix proteins that function as basement membrane components. These organotypic reconstructs of the invention are viable for about one month.

Besides growth, migration of the epithelial cells appears to be important for homeostasis of the intestinal reconstruct. Only in cultures in HGF-containing medium were epithelium cells able to cover the entire collagen matrix, consistent with evidence that this growth factor provides migratory stimulation. EGF also has been reported to stimulate migration (Basson, M. D. et al, 1992 *J Clin Invest* 90, 15–23).

Specific morphologies and states of organization were observed by growth in the base media plus 1% FCS and sub-combinations of the other factors. LIF was one of the most critical mitogens and morphogens. In the presence of LIF and EGF only, epithelial cells formed a polarized mono-layer of highly cylindrical cells. Epithelia showed disorganized and undifferentiated growth in media containing LIF, EGF and insulin. Proliferation and cell-type specific morphology were further enhanced and altered, respectively, by the combination of SCF, ET-3, EGF, and insulin. Under these conditions, epithelia formed highly disorganized structures of stratified and pseudo-stratified cells. Goblet cells lost polarity and deposited mucus towards the basement membrane.

The number of goblet cells decreased in LIF-containing media, most likely because LIF can inhibit differentiation. The dysplastic morphology and decreased number of goblet cells are early indications of pre-malignancy in the human colon (Wargovich M J. et al., 1983 *J. Natl. Cancer Inst.*, 71:125–131 and Archer, M C. et al., 1992 *Environ. Health Perspect.*, 98:195–197). In complete medium, other growth factors induced a balance between proliferation and differentiation.

In other embodiments of the organotypic culture of this invention, when the stromal matrix layer was coated with laminin 1, differentiation of the colonic epithelial cells was induced. By contrast, when the stromal matrix layer was coated with laminin 2, the cells were slower to polarize and proliferation of the cells was observed.

The intestinal reconstruct of the invention has multiple uses as discussed below. For specific uses, it is advantageous to employ growth conditions, components and media, as discussed, which produce an organotypic culture with the desired characteristics. It should further be noted that the overall size of the reconstruct can be varied. The reconstruct can be up to about 2 cm in length and up to about 7 mm thick. If desirable, the constriction level of the reconstruct can be manipulated by the amount of fibroblast introduced and the level of growth factors in the media. The standard conditions described in the examples lead to constriction of the stromal reconstruct up to about 10% of its original volume. Generally, a greater constriction results in a smaller but tougher, more easy to manipulate reconstruct, but less constriction leads to a larger and more elastic reconstruct. Reductions to 5% to 20% of the original volume are possible. Still other embodiments of the organotypic cultures of this invention are discussed below in the Examples.

III. Methods of Use of the Organotypic Culture

As discussed above, the organotypic intestinal reconstructs of the invention have multiple uses. This new reconstruction model of the normal human colon is useful in a method for identifying factors involved in the homeostatic balance of normal colonic epithelium and in its dysregulation. The results of the construction of the cultures in various supplemented media provide evidence that an imbalance of growth factors in colon epithelia contributes to transformation of the epithelium. This information thus allows for use of organotypic reconstructs in accordance with the invention for identification of compounds, molecules and growth factors or any other natural or synthetic agents that control or affect cell differentiation, proliferation, migration, malignancy, metabolism, transport, homeastasy and the like. Because they are relatively easy to generate in a reproducible manner, the organotypic cultures can be used advantageously for a number of purposes including hormone and growth factor regulatory influences as well as cell-cell and cell-matrix interactions. Other potential applications for the organotypic cultures are numerous and include the analysis of drug and nutrient transport and metabolism and the study of microorganism intestinal epithelial cell interactions.

For example, screening assays are useful to identify therapeutic agents, or to determine if agents are carcinogenic, or to allow study of drug candidates in terms of their effect on the tissue and their absorption in the tissue or localization in a type of cell or cellular compartment. A skilled artisan will readily appreciate that certain physiological or morphological embodiments of the organotypic cultures are more suitably adapted to specific purposes. The observations herein on the effect on growth, organization, polarization, generation of cell types, and movement of the cell types of the reconstruct grown in the various subsets of factors added to the minimal media allows the skilled artisan to employ a particular reconstruct in accordance to the invention.

For example, drug absorption studies may preferably utilize the organotypic culture containing small intestine epithelial cells as opposed to colonic epithelial cells, because absorption occurs predominantly in the small intestine. When evaluating an agent for its potential negative effect on cell replication, it may be advantageous to grow the organotypic reconstruct in a combination of growth factors and/or laminin-1 or laminin 2. The combination of factors is selected by the person of skill in the art to enhance or inhibit cell proliferation, or enhance or inhibit cell differentiation, depending on the specific effect expected of the drug candidate. Further for drug screening, the culture of the invention may be grown in base media plus EGF, insulin and optionally only 1% fetal calf serum (FCS), unlike the more typical complex media or minimal media fortified by higher levels of FCS, typically 10%. Lower levels of FCS in media are desired for drug screening because FCS may mask, inhibit, degrade or compete with the effects of specific drug candidates.

The agents to be tested in the various assays described below can be from any source. For example, natural or isolated factors, proteins, polypeptides or fragments, or combinations thereof, or synthetic versions thereof, chemical agents, synthetic molecules and the like, may be assayed. Food ingredients may also be assays. Synthetic chemicals, biochemicals, or library of factors can be tested. The agent tested may be labeled for convenience of detection and/or isolation. Labeling can be by any method known in the art, example by conjugation labeling, by radiolabeling or by addition of an affinity tag sequence to the primary sequence (for example a His amino acid sequence to the end of a protein sequence). Alternatively, an unlabeled factor can be detected after the assay, by immune assays, enzymatic assays, or metabolic assays. The selection of the label, and the type of detectable assay (e.g., immunoassays, enzymatic assays and the like) to further detect the agent's presence in the culture over time, may be readily selected by one of skill in the art.

Thus, in one embodiment, a method of in vitro screening of an agent can be accomplished by contacting an organotypic culture of this invention with the agent in a vessel, and observing the effect of the agent upon the culture. For example, in one such method, the agent is a drug candidate, and screening includes determining the absorption rate of the drug candidate by measuring and observing the movement of the drug candidate through the epithelial cell layer at the top of the culture, optionally as a function of time.

In one embodiment, an assay that permits screening for absorption of a drug candidate employs the organotypic culture prepared with human small intestinal cells, seeded on an artificial stroma coated with a matrix protein, e.g., Laminin-1 or Laminin-2. Preferably, the reconstruct would be grown in complete media. Depending on the identity of the drug candidate, it may be labeled with a conventional detectable label. Alternatively, an enzymatic assay or immunoassay is available to detect the drug candidate. When the epithelial cells are still young but well developed on the culture (about 5 days after seeding), the drug candidate is spotted on a small surface area on top of the reconstruct. The culture is observed. The presence of the drug appearing at the bottom of the vessel in which the reconstruct is grown or in cells isolated from the reconstruct at a site away from the application site, as detected by the label, enzymatic assay or immunoassay, is indicative of absorption. In an alternative embodiment, the drug candidate is placed at the growth vessel at the bottom of the culture and its detection in epithelial cells at the top of the culture is similarly monitored. In still another embodiment of a screening assay, the rate of absorption is determined in time controlled experiments.

Another screening assay involves screening the agent for toxicity to human intestinal tissue. In this embodiment of the method, the observing step involves observing the effects of the agent on the morphology and life span of the epithelial cells, whereby an agent which reduces the life span of the epithelial cells or has a negative impact on the morphology of the epithelial cells is toxic. Similarly, the screening methods of this invention can include screening the agent for its effects on hormone regulation in the culture or screening the agent for binding for a receptor in the culture.

Still another use of the organotypic culture of this invention is in a method for screening an agent for repairing effect on intestinal epithelial cell injury. According to this type of assay, the layer of epithelial cells on an organotypic culture is disrupted. The site of disruption is contacted or exposed to the agent. Observing the effects of the agent on the repair of the epithelial cell layer permits a determination that an agent which promotes repair of the epithelial cell layer is capable of repairing the injury. In one embodiment, such an assay to screen for agents that can promote healing of a wound in a colonic/intestinal tissue employs an organotypic culture of this invention that was grown in the complete media and, preferably, has an artificial stromal layer that was coated with Laminin-1 and/or Laminin-2. When still young but well developed (about day 4), the organotypic reconstruct would be wounded. The wound could be made mechanically (a scratch), or by a temporary/local exposure to an acid or to a base, or a virus, etc. The wounded reconstruct would be allowed to recover in the presence of a drug candidate. Proper controls may include a similarly constructed and damaged reconstruct left without treatment. Comparison of the rate of repair and the final repair condition of the treated culture vs. the control culture would permit identification of a suitable therapeutic agent.

In another example, an assay is designed for screening for agents that can promote healing of a malignancy and destroy or inhibit growth of malignant cells in colonic/intestinal tissue. The organotypic culture useful in this invention would be the embodiment described above which is additionally seeded on the surface of the artificial stroma with a malignant cell type, for example a cancerous or malignant tumor cell. Once the tumor cell is developed on the organotypic culture, the culture is contacted with the agent. The effect of an agent or a drug candidate on the proliferation, growth or general morphology of the malignant cell type would be observed. Proper controls may include a similarly constructed and seeded or implanted reconstruct left without treatment by the drug candidate.

Still another example of a screening assay of this invention involves studying the effect of an agent, for example an environmental factor or a food type, on the proliferation, differentiation or survival of cells in the culture. For the study of differentiation, the embodiment of the organotypic culture that may be used optionally contains the stroma coated with Laminin-1. If the effect on cell proliferation is to be studied, the culture may be advantageously grown in a minimal medium (EGF, insulin, 2% FCS).

One of skill in the art will recognize other possible assays, including assays that use multiple agents to determine their combined effects on the organotypic culture, and the preferred embodiment of the organotypic culture to elucidate the specific question of the assay.

In another embodiment, the culture of this invention is useful in a method for enhancing epithelial cell repair at an in vivo site of intestinal or colonic injury. According to this method, at least one of collagen, fibroblasts, at least one growth factor that binds the IGF-1 receptor, at least one growth factor that binds the EGF receptor, and LIF, and a combination thereof are delivered to the site of the injury. The delivery can include administering to the site of the injury at least one recombinant vector comprising a polynucleotide molecule encoding at least one of a growth factor that binds the IGF-1 receptor, a growth factor that binds the EGF receptor, a growth factor that binds the LIF receptor, or a combination thereof. The vector may be present in a transfected or infected fibroblast delivered to the site of the injury. The vector may be present in transfected or infected intestinal or colonic epithelial cells delivered to the site of the injury. The methods of delivery may be selected by the attending physician with regard to the nature of the injury, and the particular therapeutic composition being administered. However, it is anticipated that local administration would be preferred. The amounts and dosages of such vectors or organotypic components would also be selected by one of skill in the art.

Still another use of the culture of this invention is in treating an intestinal wound by placing an organotypic culture on the intestinal wound in a patient, i.e., using the culture as a tissue replacement in a surgical procedure. Preferably at least one cell present in said organotypic culture is allogeneic to the patient receiving treatment. This method is useful in treating wound is caused by, inter alia, chronic inflammation, Crohn's disease, ulcerative colitis, intestinal hemorrhage, hemorrhaging diarrhea, ulcers, or a malabsorption syndrome. Such wounds may also be the result of surgery, e.g., a post operative wound, or irradiation, e.g., a post irradiation treatment.

Typically the reconstruct used for treatment would be one that most closely resembles the in situ tissue. In that respect, a treatment would preferably employ a reconstruct made by the seeding of small intestine cells. Preferably, the reconstruct would be grown on the complete media. In accordance with another embodiment, at least one of the cell types used to construct the intestinal reconstruct is allogeneic, i.e., derived from the patient who will receive treatment.

The following examples are provided to illustrate the invention and do not limit the scope thereof. One skilled in the art will appreciate that although specific reagents and conditions are outlined in the following examples, modifications can be made which are clearly encompassed by the spirit and scope of the invention, which modifications do not involve undue experimentation on the part of the person of skill in the art.

EXAMPLE 1

Preparation of Organotypic Cultures

A. Cells

Human colonic fibroblasts were established from explants of colons from 7- to 20-week-old fetuses of therapeutic or spontaneous abortions. The colonic explants were obtained through Advanced Bioscience Resources (Alameda, Calif.), after approval by the Institutional Review Board. Out of three fibroblast cell lines established from these explants, FFC331 was used for most of these studies. The fibroblasts were cultured in Dulbecco's modified minimum essential medium (DMEM, GIBCO BRL, Rockville, Md.) supplemented with 10% fetal calf serum (FCS, Cansera, Rexdale, Ontario, Canada) and antibiotics. Cultures were used up to passage 10.

Human smooth muscle cells (HIAS 119) were isolated from large vessels and maintained in medium M199, supplemented with 10% FCS, 2 mM L-glutamine, and 50 µg/ml of bovine hypothalamic extract (Sorger, T. et al. 1995 *In Vitro Cell Dev. Biol. Anim.*, 31:671–683).

Human enteric epithelial cells were isolated by dissociation from the colon specimens within 24 hr after surgery. The colon lumen was opened and washed in Hank's buffered salt solution (HBSS; Gibco BRL) supplemented with penicillin at 200 U/ml, streptomycin at 200 µg/ml (30-002-CL, Cellgro, Herndon, Va.) and gentamycin at 100 µg/ml (30-005-CR, Cellgro). After removal of the serosa, the remaining tissue was incubated for 10 min in HBSS containing 20 mg/ml Mucomyse (N-acetyl-L-cystein; Sigma, St. Louis, Mo.), pH 7.2, to remove surface-bound mucin. After three washings, the tissue was dissociated at 37° C. in HBSS without calcium and magnesium (GIBCO BRL), supplemented with 1 mg/ml D-glucose (Sigma) and 1 mM ethylene diaminetetraacetic acid (EDTA; Sigma). After 10-minute incubation with occasional shaking, single cells and small cell clusters were removed and collected in a 2-fold volume of base medium supplemented with 5% FCS. The procedure was repeated twice. All collected epithelia were pelleted at 800×g for 10 minutes. Single cells and cell clusters were washed and then resuspended in complete growth medium.

B. Media

Base medium consisted of 4 parts of MCDB 201 medium and 1 part of L15 medium (Sigma), 5 µg/ml of transferrin (Sigma), and 50 g/ml of streptomycin and gentamycin, respectively. Complete growth medium consisted of base medium supplemented with recombinant human basic fibroblast growth factor (bFGF) at 10 ng/ml, human recombinant epidermal growth factor (EGF) at 10 ng/ml (Sigma), insulin at 5 pg/ml (Sigma), endothelin-3 (ET-3; Peninsula Labs, San Carlos, Calif.) at 264 ng/ml, hepatocyte growth factor (HGF; R&D Systems, Minneapolis, NIN) at 30 ng/ml, leukemia inhibitory factor (LIF; R&D Systems) at 0.2 ng/ml, stem cell factor (SCF; Sigma) at 30 ng/ml, autocrine motility factor (AMF, Sigma) at 35 ng/ml, and 1% FCS (Nesbit M., et al. 1999 *Oncogene* 18:6469–6476).

To determine the role of growth factors on proliferation of colonic epithelial cells, this growth medium was modified by changing combinations of growth factors and deleting serum. Keratinocyte growth factor (KGF, R&D Systems) at 20 ng/ml was also tested as part of 23 growth factor combinations.

C. Preparation of the Organotypic Culture.

In this embodiment and others in which smooth muscle cells are introduced into the artificial stroma, the artificial stroma is generally produced by mixing fibroblasts and smooth muscle cells in a 10:1 ratio within the collagen. Specifically, collagen gels with embedded colonic fibroblasts and smooth muscle cells (also referred to as artificial stroma or stromal reconstructs) were obtained by suspending bovine tendon acid-extracted collagen (Organogenesis, Canton, Mass.) to a final concentration of 0.9 to 1.1 mg/ml in DMEM supplemented with Vitamin C (Sigma) at 50 µM/L, L-glutamine (GIBCO-BRL) at 1.66 mM and 1% FCS. The suspension was neutralized, pH 7.2, with 7.5% sodium bicarbonate. Before the collagen gel hardened, colonic fibroblasts ($2 \times 10^5$/ml) and smooth muscle cells ($2 \times 10^4$/ml) were added. Chambered slides, Lab-Tek 8 or Lab-Tek 16 wells (Nalgene Nunc International, Rochester, N.Y.) were filled with 0.3 and 0.2 ml of the collagen/cell mixture, respectively.

Single epithelial cells and small cell clusters were freshly isolated from the mucosa of fetal colon using mild EDTA treatment. After solidification of the artificial stroma, these freshly isolated colonic epithelial cells in medium were seeded on the surface of the stroma to establish the organotypic culture. Specifically, the cultures were prepared by seeding epithelial cells in 0.4 ml of complete growth medium. After seeding, epithelia were incubated for 60–90 minutes in a low volume of medium (50–100 µl) to enhance attachment. The base medium of MCDB201/L15 with transferrin and antibiotics was supplemented with EGF, Insulin, HGF, bFGF, ET-3, LIF, SCF, AMF, and 1% FCS. The colonic cells began attaching within 60 minutes unless they were surrounded by mucin.

D. Characterization of Organotypic Cultures.

For evaluation of proliferation, cell proliferation labeling reagent (Amersham, Pharmacia Biotech, Inc., Piscataway, N.J.) was added to the medium according to the manufacturer's instructions. Harvested cultures were fixed in 1.5% paraformaldehyde followed by characterization, embedded in paraffin for sectioning and processed for microscopy. For electron microscopy, they were fixed in 4% glutaraldehyde.

For histochemistry and immunohistochemistry, 5 µm thick sections were cut from the paraffin beds and stained with hematoxylin and eosin (H&E), PAS, or Alcian Blue using standard procedures. Antibodies for staining were against bromodeoxyuridine (BrdU, Amersham Pharmacia Biotech, Inc, Piscataway, N.J.), the proliferation marker Ki67 (DAKO, Carpinteria, Calif.), and α-SMA (Sigma). Immunohistochemistry was performed using standard protocols.

Total relative cell numbers of a specific type were counted as an average of all nuclei counts from a minimum of 3 randomly selected cross-sections of a reconstruct. Goblet cells were counted based on their typical morphology and positive Alcian staining in at least 3 randomly selected slides. Proliferation rates in % were established by counting the number of BrdU or Ki-67-positive nuclei per total epithelial cell nuclei of section. Apoptotic cells were counted in H&E-stained sections (Vagunda, V. et al. 2000 *Anal. Quant. Cytol. Histol.,* 22:307–310). Apoptotic bodies and nuclei were determined according to the size and numbers of the fragments. Apoptosis was calculated as percentage of total nuclei per section (Kerr, J F. et al. 1972 *Br. J. Cancer,* 26:239–257)

E. Results of Characterizations

In the first embodiment of the organotypic culture described above, spreading of cells from clusters was seen after 12 hours. The tissue-like/structure was formalin-fixed 12 hours after seeding, and then sectioned and stained with hematoxilin and eosin (H&E). A cluster of epithelial cells attached in the middle of the culture, and flat cells began covering the free surface. After 24 hours, the cells had migrated over the entire matrix and formed a flat monolayer. At this time, the collagen began to shrink due to contraction by the fibroblasts and smooth muscle cells. Maximum shrinkage was reached by day 3. The reconstructs at this point were 3 mm long and about 1.5 mm thick. Day 4 after seeding an epithelial monolayer of polarized colonic cells has formed. Goblet cells are dispersed throughout the epithelial layer. Fibroblasts and smooth muscle cells are found throughout the organotypic culture. The artificial stroma has constricted to approximately 10% of its original volume. With contraction of the collagen matrix, a change of the epithelial phenotype occurred, from flat on day 1 to cuboidal and columnar on day 4.

By day 10 after seeding, a continuous, well-polarized epithelial layer had covered all sides of the organotypic culture. Fibroblasts and smooth muscle cells remained dispersed throughout the collagen, but some fibroblasts migrated towards the epithelial layer and closely aligned below it. Mucin-producing goblet cells, identified by their morphology and Alcian blue positive staining, were dispersed throughout the epithelial cell layer. In complete growth medium, the percentage of goblet cells remained stable until day 10. By day 20, the monolayer of epithelial cells remained intact but the internuclear distances increased. Goblet cells were still present by day 28, when the total cell number had decreased.

Electron micrographs of the colon epithelium in organotypic culture demonstrated formation of well-developed microvilli on the apical surface of the epithelial cells. The upper lateral margins of the epithelial cells were connected by tight junction complexes. Intercellular adhesion complexes were formed by desmosomes and interdigitating folds. Brush borders and tight junctions were also identified in mucin-producing goblet cells. Neuroendocrine cells were filled with neurosecretory vesicles and lysosomes. Between the epithelial and mesenchymal layers, an immature basement membrane developed.

Immunohistochemistry of the organotypic culture 10 days after seeding by staining for the presence of α-SMA showed positive fibroblasts, identified by their rough endoplasmic reticulum, tightly aligned subjacent to the basal side of the epithelial cells. These fibroblasts resembled intestinal subepithelial myofibroblasts, regardless of whether a mixture of fibroblasts and smooth muscle cells or only fibroblasts were used for the artificial stroma. Only cells adjacent to the epithelium were positive for α-SMA. In a section of the fetal colon, similarly stained for α-SMA, an alignment of stained mesenchymal cells were observed beneath the epithelial layer of the myofibroblasts below the crypts.

Two to 3% of epithelial cells on the stromal reconstructs stained positive for the proliferation markers Ki67 and BrdU on day 10, and 4.5% of the epithelial cells visible in the sections appeared apoptotic.

In control cultures, colonic epithelial cells were seeded on plastic dishes coated with collagens I and III or Matrigel matrix, defined above. The colonic epithelial cells remained flat and died within 8 days. In co-cultures of fibroblasts, smooth muscle cells, and epithelial cells, colonic epithelial cells were overgrown by fibroblasts and smooth muscle cells and died after a few days.

EXAMPLE 2

Growth Factor Modulation of the Epithelial Phenotype

To define the role of critical growth factors supporting growth and differentiation of the enteric epithelial cells, an organotypic culture, such as that described in Example 1, was grown in medium in which the number of supplements was reduced.

In one experiment the base medium (MCDB 201/L15 medium with transferrin and antibiotics) was supplemented with EGF and insulin. In the resulting organotypic culture on day 3, undifferentiated colonic epithelial cells attached to the artificial stroma, but they were not polarized. On day 7, in the presence of EGF and insulin, viable, non-polarized, epithelial cells survived in isolated small clusters with round-shaped undifferentiated morphology on the artificial stroma.

In other experiments, the growth factors, including insulin, EGF, SCF, ET-3, KGF, bFGF, or AMF were added individually to the base medium (MCDB 201/L15 medium with transferrin and antibiotics). In each case, epithelial cell proliferation was not supported in the organotypic culture.

In still other experiments, base medium was supplemented with EGF, insulin, and LIF. By day 3, flat epithelial cells are migrating on the artificial stromal and form a monolayer covering the surface. On day 7, the colonic epithelial cells form highly cylindrical, polarized epithelial clusters. Mesenchymal fibroblasts closely underline the epithelial layer, but goblet cells were absent.

In another experiment, the epithelial cells were cultured in base medium supplemented with HGF, AMF, insulin, and 1% FCS. The resulting organotypic culture by day 4 had a flat, differentiated monolayer, which covers the entire artificial stroma.

In another experiment, the organotypic cultures were prepared by seeding epithelial cells on the artificial stroma in complete medium C or medium L/S/E or medium L. Medium C contained transferrin, insulin, bFGF, EGF, ET-3, HGF, LIF, SCF, AMF, and 1% FCS as supplements. L/S/E medium contained transferrin, insulin, LIF, SCF, ET-3, EGF, and 1% FCS. L medium contained transferrin, insulin, LIF, EGF, and 1% FCS. Sections of the cultures were stained with H&E and Alcian blue after 12 hours (day 0) and 4 days. Values were generated SD of 5 fields from 2 independent experiments. The numbers of cells attached on day 0 between the three groups were not significantly different. On day 4, using epithelial cell numbers in complete medium C for comparison, the numbers of epithelial cells were significantly higher in L/S/E and L media (p<0.001). The L/S/E-supplemented base medium (LIF, SCF, ET-3, EGF, insulin, and 1% FCS) induced formation by day 4 of highly disorganized structures of stratified and pseudostratified epithelial cells. The epithelium was hyperplastic with morphological atypia. In contrast to results obtained with complete growth medium, only the upper surface rather than the entire artificial stroma was covered with epithelium. The combination of LIF, SCF, ET-3, EGF, insulin and 1% FCS stimulated formation of an epithelial layer with the highest cell numbers which were approximately double compared to complete medium This growth-inducing medium L/S/E stimulated the formation of goblet cells similar to those formed in complete growth medium. However, the number of goblet cells in L/S/E medium was significantly lower than those in complete medium ($p<0.02$) but not lower than those in C-medium ($p<0.07$).

EXAMPLE 3

Role of Extracellular Matrix (ECM)

Another embodiment of an organotypic culture prepared as described substantially as in Example 2, has an additional component. An extracellular matrix was applied to the organotypic cultures by coating the artificial stroma with matrix proteins Laminin-2 $\alpha 2\beta 1\gamma 1$ (Life Technologies, Rockville, Md.), Laminin-1 $\alpha 2\beta 1\gamma 1$ (Sigma), or Matrigel® gel matrix (Collaborative Research, Bedford, Mass.), which contains Laminin-1 and other matrix proteins, such as collagen IV and nitrogen (Burgeson, R E., et al. 1994 *Matrix Biol.*, 14:209–211 and Page, KC. et al. 1990 *J. Biol. Reprod.*, 43:659–664).

Fifty to 100 μl of base medium containing 20 ng/ml of laminins were added onto the surface of the artificial stroma for 60 minutes at 37° C. Matrigel® matrix was diluted 1:5 to 1:10 in base medium before use. After incubation, unbound laminins or Matrigel® matrix were removed by two washings with base medium. The organotypic cultures were incubated at 37° C. in 5% $CO_2$ in growth medium, which was changed daily for 7 days, then three times per week for an additional 21 days.

Growth and differentiation of colonic epithelium in growth medium was regulated by ECM components at the interface between the stroma and the epithelial layer. These ECM experiments were done in base medium, supplemented with LIF, SCF, ET3, EGF, insulin, and 1% FCS. Coating of the artificial stroma (i.e., collagen and cellular) matrix with Matrigel matrix and purified laminins increased adhesion and spreading. The epithelial cells and clusters attached within 15 minutes and spread within 30 to 60 minutes. When one portion of the artificial stroma was coated with Matrigel matrix, which contains Laminin-1, and the other with purified Laminin-2, cells formed matrix-specific phenotypes.

Quantitative analysis of the growth fractions confirmed that the different laminins control growth and differentiation. Laminin-1, either as purified matrix protein or when present in Matrigel matrix, induced differentiation, whereas Laminin-2 stimulated cell growth. Enteric epithelial cells spread similarly on substrates of Laminins-2 and —I bound to plastic of culture dishes. However, by day 5, the epithelial cells survived only with Laminin-2 as substrate and not with Laminin-1. The colorectal carcinoma cell line HT29 showed similarly better growth on Laminin-2 when compared to Laminin-1.

EXAMPLE 4

Organotypic Cultures of Normal Human Enteric Epithelium

The following experiments provide more recent data on the generation of these organotypic cultures of the invention.

A. Isolation Of Colonic Epithelial Cells.

Human enteric epithelial cells were isolated from fetal colon obtained after therapeutic or spontaneous abortions at 17–21 weeks' gestation. Specimens were received through Advanced Bioscience Resources (Alameda, Calif.) after approval by the Institutional Review Board. The colon lumen was opened and washed in Hank's buffered salt solution (HBSS; Gibco BRL, Rockville, Md.) supplemented with penicillin (200 U/ml), streptomycin (200 μg/ml) (Cellgro, Herndon, Va.) and gentamycin (100 μg/ml) (Celigro). After removal of the serosa, the tissue was incubated for 10 minutes in HBSS containing 20 mg/ml Mucomyst® (N-acetyl-L-cysteine; Sigma, St. Louis, Mo.), pH 7.2, to remove surface-bound mucin. After three washings, tissue was dissociated at 37° C. in HBSS without $Ca^{++}/Mg^{++}$ (GIBCO BRL), supplemented with 1 mg/ml D-glucose (Sigma) and 1 mM ethylene diaminetetraacetic acid (EDTA; Sigma). Isolated colon mucosa was dissociated into single cells and small cell clusters. The epithelial layer was stripped, including the bottom of crypts.

After 10-minute incubation with occasional shaking, these single cells and small cell clusters were removed and collected in a two-fold volume of base medium supplemented with 5% fetal calf serum (FCS). Base medium consisted of 4 parts MCDB 201 medium and 1 part L15 medium (Sigma), supplemented with 2 ng/ml human recombinant EGF (Sigma), 5 μg/ml insulin (Sigma), 5 μg/ml transferrin (Sigma), 50 μg/ml streptomycin and gentamycin, respectively, and 2% FCS. The procedure was repeated twice. All samples were pelleted at 800×g for 10 minutes.

These single cells and cell clusters were washed and resuspended in complete growth medium base medium supplemented with 10 ng/ml human recombinant basic fibroblast growth factor (bFGF) (Nesbit, M. et al, 1999 *Oncogene*, 18, 6469–6476), 264 ng/ml endothelin-3 (ET-3; Peninsula Labs, San Carlos, Calif.), 30 ng/ml hepatocyte growth factor (HGF; R&D Systems, Minneapolis, Minn.), 0.2 ng/ml LIF (R&D Systems), 30 ng/ml stem cell factor (SCF; Sigma), and 35 ng/ml autocrine motility factor (AMF; Sigma).

B. Isolation of Fibroblasts.

Human colonic fibroblasts were derived from colon explants from 17- to 21-week fetuses. Fibroblasts of three specimens were cultured in Dulbecco's modified minimum essential medium (DMEM; GIBCO BRL) supplemented with 10% FCS (Cansera, Rexdale, Ontario, Canada) and antibiotics. Cultures were used up to passage 10.

Human smooth muscle cells HIAS119, kindly provided by Dr. E. Levine, The Wistar Institute, were isolated from large blood vessels and maintained in medium M199, supplemented with 10% FCS, 2 mM L-glutamine, and 50 μg/ml bovine hypothalamus extract (Oda, D. et al, 1998 *In Vitro Cell. Dev. Biol. Anim.*, 34, 46–52). Fibroblasts at $8\times10^5$/ml were embedded in collagen type I (Organogenesis, Canton, Mass.) to a final concentration of 0.9 to 1.1 mg/ml in DMEM supplemented with 50 μM vitamin C (Sigma), 1.66 mM L-glutamine (GIBCO-BRL), and 1% FCS. The suspension was neutralized, pH 7.2, using 7.5% sodium bicarbonate. Chambered slides, Lab-Tek 8 wells (Nunc International, Rochester, N.Y.), were filled with 0.2 ml of the collagen and cell suspension. In initial experiments, fibroblasts were seeded together with smooth muscle cells ($2\times10^4$/ml).

C. Preparation of the Organotypic Culture

Colonic epithelial cells described above were seeded on top of collagen gels containing embedded fibroblasts described above in 0.4 ml of complete growth medium. After seeding onto the matrix of collagen type I with embedded fibroblasts, samples were incubated at 37° C. in 5% $CO_2$ for 60–90 minutes in a low volume of medium (50–100 μl) to enhance attachment. The epithelial cells and clusters attached within 60 minutes. The wells were then filled with complete growth medium. Medium was changed daily for 10 days, then three times per week for an additional 21 days.

D. Characterization of the Culture

Proliferation of organotypic cultures was determined by adding bromodeoxyuridine (BrdU) to the medium according to the manufacturer's instructions (Amersham Pharmacia Biotech, Inc., Piscataway, N.J.). Thymidine incorporation was measured in cells, incubated with 1 µCi $^3$H-thymidine/well for 18 hours before harvest and determination of radioactivity.

The organotypic cultures were characterized as follows. Harvested organotypic cultures were fixed in 1.5% paraformaldehyde and embedded in paraffin. For electron microscopy (EM), cultures were fixed in 4% glutaraldehyde. For histochemistry and immunohistochemistry, 5-µm thick sections were cut from the paraffin beds and stained with hematoxylin and eosin (H&E) or Alcian Blue using standard procedures.

Goblet cells were detected using Alcian Blue and EM. Enteroendocrine cells were identified by chromogranin A staining and EM. Immunohistochemical staining was done with monoclonal antibodies specific for: BrdU (Amersham), Ki67 (DAKO, Carpinteria, Calif.), α-smooth muscle actin (SMA) (Sigma), cytokeratin 19 (CK 19; antibody BA17 [33] kindly provided by Dr. J. Kovarik, Brno, Czech Rep.), chromogranin A (Novocastra, New Castle Upon Tyne, UK) and carbonic anhydrase II (The Binding Site Limited, Birmingham, UK). Immunohistochemistry was performed by standard techniques as described (Dai, C. Y. et al, 2000 Gastroenterology, 119, 929–942). Alkaline phosphatase activity of paraffin-embedded samples was detected using colorimetric substrate (AP Substrate Kit, SK 15100, Vector, Burlingame, Calif.).

Cell numbers were determined per high-power field (0.11×0.18 mm) using 40× magnification as the mean (±SD) of 364 measurements. Constriction of collagen matrices was measured as the length of the longitudinal axis of collagen harvested on days 0.5, 4 and 10 (mean±SD of 32 measurements of 4 samples. Positive cells per area were counted in 12 consecutive fields per cross-section (mean±SD of 16 areas of 2 random cross-sections from 4 samples. Relative number of positive cells per area was expressed as mean±SD of positive/total cells from 16 areas of 2 random cross-sections for each sample. Statistical significance was tested using Student's t-test.

In these cultures colonic epithelial cells attached within 60 minutes. The cells began spreading from clusters at 6 hours after seeding (FIG. 1) and migrated to cover the entire matrix. Constriction of collagen by the fibroblasts started after 24 hours and was maximal by day 4 when the matrix had shrunk to approximately 40% of its original volume (FIG. 1).

Because initial experiments with a mixture of fibroblasts and smooth muscle cells (10:1) revealed no alteration of constriction or properties of the epithelial cells, all subsequent analyses were performed with fibroblasts only, which remained viable throughout the experiments. As the collagen matrix constricted, epithelial cell morphology changed from flat during the initial migratory phase to polarized and columnar by day 4. Mucin-producing goblet cells, based on their morphology and Alcian blue-positive staining, distributed throughout the epithelial cell layer. Fibroblasts migrated closely underneath the epithelial layer. The 4 day reconstruct is partially covered by the epithelial layer. After 10 days, epithelial cells covered all sides of the collagen matrix. The epithelial layer was continuous and well-polarized. At this time, 2–10% of epithelial cells stained positive for the proliferation marker Ki67 and up to 70% had incorporated BrdU when continuously added to the medium starting at the time of seeding. Total cell numbers began to decrease by day 20 when cells flattened. Mucin-producing goblet cells, identified by their typical round morphology and staining with Alcian Blue, were distributed throughout the epithelial cell layer. The percentage of goblet cells in the layers remained stable until day 10 and individual cells had incorporated BrdU, but their total number decreased together with a decrease in all epithelial cells.

Fibroblasts remained dispersed throughout the collagen. Fibroblasts migrating toward the epithelial cell layer expressed α-SMA as a myofibroblast marker. α-SMA-positive intestinal subepithelial myofibroblasts were also seen in normal fetal human colon (control). Cells grown in monolayer or on a collagen matrix without fibroblasts did not proliferate on day 4 as determined by $^3$H-thymidine incorporation assay and Ki67 immunohistochemistry, and they flattened and died by day 8 at the latest.

EM analysis of the colonic epithelium in organotypic culture (10 day) revealed absorptive enterocytes with brush border, apical junctional complexes with tight junction, desmosomes, interdigitating folds, immature basement membrane depositions and underlying mesenchymal cells, with rough endoplasmic reticulum and formation of regular brush border. Well-developed microvilli were observed on the apical surface of the epithelial cells. The upper lateral margins of all epithelial cells were interconnected by tight junctions. Intercellular adhesion complexes were formed by desmosomes and interdigitating folds. Brush borders and tight junctions were identified in mucin-producing goblet cells with mucin-containing granules. Fibroblasts closely underlay the epithelium, with immature basement membrane. Specific vesicles and lysosomes were located close to the base identified enteroendocrine cells, as confirmed by chromogranin A immunohistochemistry (see FIG. 6C). Between the epithelial and mesenchymal layers, an immature basement membrane developed. Fibroblasts, identified by their extensive rough endoplasmic reticulum, aligned below the basal side of the epithelial cells so that each epithelial cell was underlined by a fibroblast. Such thin layers of fibroblasts were absent in collagen surface areas free of epithelial cells. Neurosecretory cell containing specific vesicles and larger secondary lysosomes with underlying fibroblasts were also observed Growth factors modulated epithelial cell growth and differentiation. Epithelial cell growth and differentiation in the organotypic culture was achieved with complete growth medium of MCDB 201/L15 supplemented with EGF, insulin, transferring, bFGF, ET-3, SCF, HGF, LIF, AMF, and 2% FCS. No single growth supplement sustained cell survival.

Base medium supplemented with EGF, insulin and transferring allowed survival of cells for up to 7 days. Additional growth factors in the base medium altered morphology, differentiation and/or growth patterns of cells, inducing two distinct phenotypic patterns of the epithelial cells. Base medium containing EGF, insulin, transferring and 2% FCS supplemented with HGF and AMF induced a flat, cuboidal cellular phenotype and the cells expressed the differentiation marker carbonic anhydrase II (identified by staining), which marker is found in the upper crypts and villi in normal colon. Base medium supplemented with LIF, ET-3, and SCF induces disorganized, multi-layered epithelium of stratified and pseudo-stratified cells. The presence of LIF, ET-3, and SCF in the medium induced thickening of the colonic cell layer and inhibited expression of carbonic anhydrase II. Epithelial cells in both growth media expressed cytokeratin 19, which is found throughout the normal human colon, whereas alkaline phosphatase expressed in the upper crypts of normal colon was not detected.

When only LIF was added to base medium (day 3), the cells flattened and migrated to form a monolayer. On day 7, the proliferating epithelial cells show polarization with fibroblasts underlying the epithelial layer. LIF-stimulated cultures formed disorganized structures of stratified and semi-stratified cells that did not express the differentiation marker carbonic anhydrase II.

Control cultures maintained in the absence of LIF remained round, and poorly attached by day 3, and cell numbers remained low, indicating little proliferation by day 7. In the control cultures with no fibroblasts in the collagen matrix, LIF could not sustain epithelial cell survival, resulting in cell death. Epithelial cells did not survive in the absence of both LIF and fibroblasts.

Figure 2A:
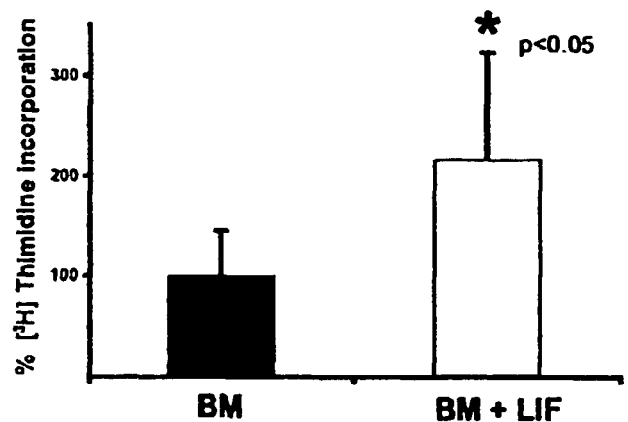
FIG. 2A is a bar graph illustrating the results of $^3$H-thymidine incorporation assays on organotypic cultures of the invention grown in variously supplemented media, as discussed in Example 4. Significant stimulation of cells in base medium with LIF (BM+LIF) is compared with base medium (BM) only. Incorporation was measured after 2 days when cells were cultured on matrix without fibroblasts. Results are mean (±SD) median of 4 experiments.
Figure 2B:
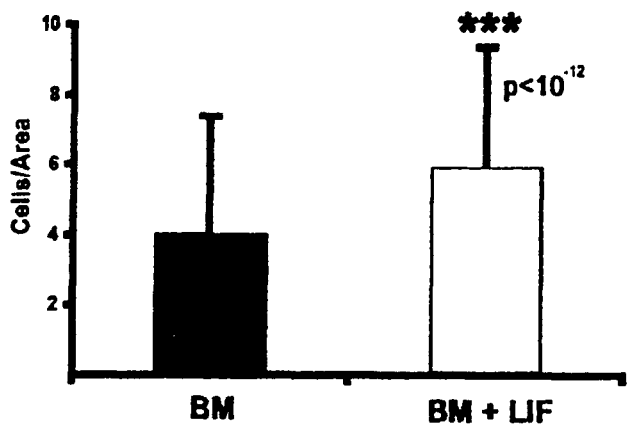
FIG. 2B is a bar graph illustrating that the number of colonic epithelial cells is significantly higher in LIF-containing base medium. Results are mean (±SD) from 360 fields.
Figure 2C:
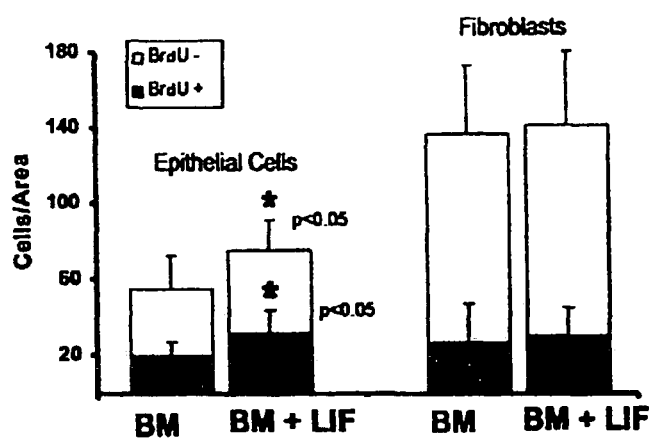
FIG. 2C is a bar graph illustrating that numbers of both BrdU-positive and total epithelial cells were significantly higher in LIF-stimulated cultures, whereas there were no differences in fibroblast numbers.

Base medium with LIF and 2% FCS allowed migration of the epithelial cells around the entire matrix by day 7, whereas cells in the absence of LIF covered only a portion of the matrix by day 7. Growth of epithelial cells was significantly stimulated by LIF (FIGS. 2A–2C). Cells showed significant incorporation of BrdU (indicating proliferation of both fibroblasts in collagen and surface epithelial cells) and $^3$H-thymidine (FIG. 2A), with increased cell numbers/area (FIG. 2B). The stimulation of DNA replication and cell proliferation was solely attributable to LIF-mediated stimulation of epithelial cells and not of fibroblasts (FIG. 2C), LIF did not change collagen constriction by fibroblasts.

Figure 3A:
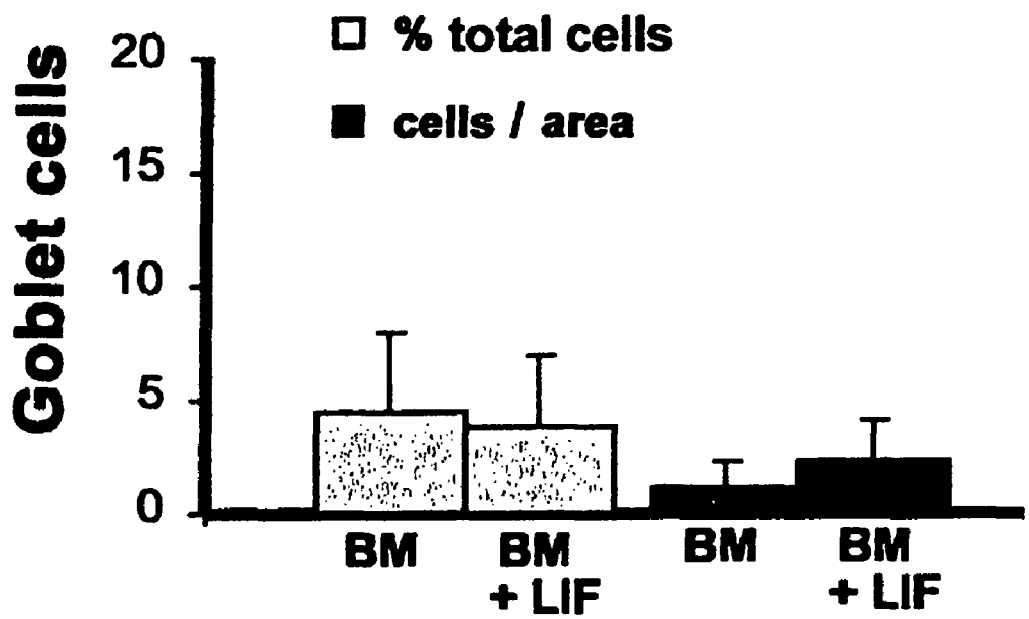
FIG. 3A is a bar graph illustrating differentiated cells in organotypic colon cultures, showing a percentage of goblet cells among total cells and per area, indicating lack of stimulation by LIF. There was a trend (p=0.10) toward increased absolute numbers of goblet cells in LIF-stimulated cultures.
Figure 3B:
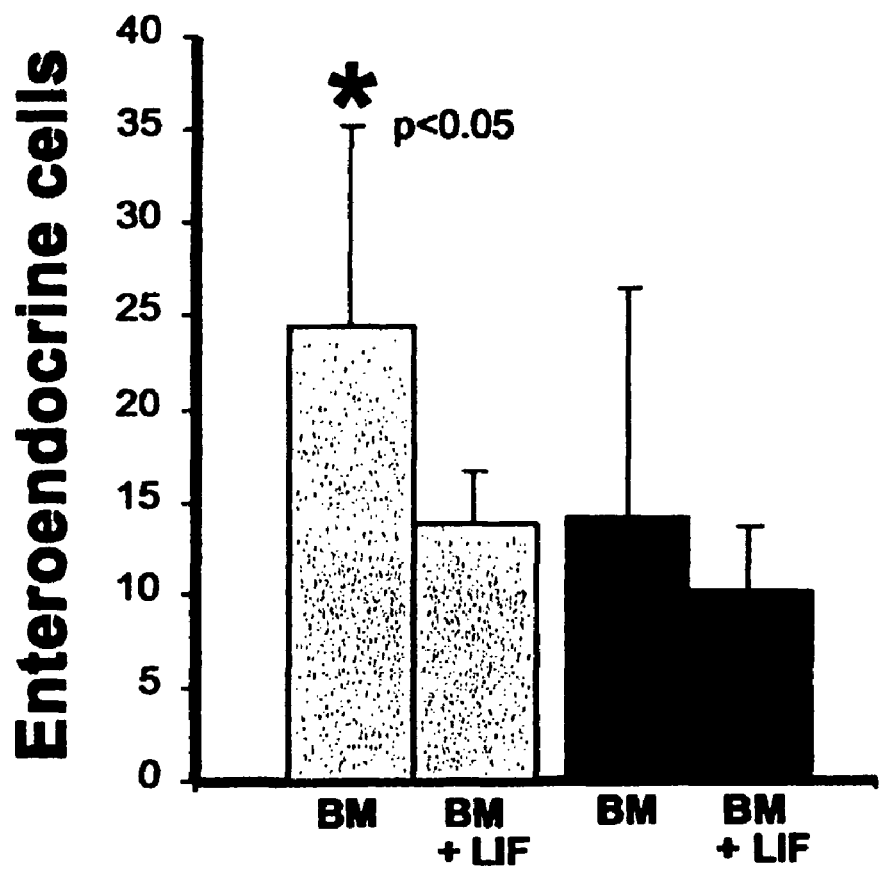
FIG. 3B is a bar graph illustrating differentiated cells in organotypic colon cultures, showing a decrease of total enteroendocrine cell numbers in LIF-containing medium.

Double staining of organotypic cultures with BrdU and Alcian blue identified differentiated cells in organotypic colon cultures, including proliferating goblet cells. Goblet cells represented approximately 4% of all enterocytes, but differences in relative numbers of LIF-cultured versus control base medium cultured cells were not significant (3.8±3.5% versus 4.2±3.2%, p=0.81) (FIG. 3A). There was a trend toward increased numbers of goblet cells per area in LIF-stimulated samples (2.25±1.66 versus 1.25±0.99 in samples without LIF, p=0.13). Cells cultured for 10 days in the presence of BrdU and stained for Alcian blue showed that approximately 33% of the goblet cells had proliferated during this time period. By contrast, relative numbers of enteroendocrine cells were significantly decreased in the presence of LIF (FIG. 3B). Cultures labeled for 10 days with BrdU, stained and then counterstained with chromogranin A for detection of enteroendocrine cells revealed no proliferating enteroendocrine cells.

All references cited above as well as U.S. provisional patent application No. 60/314,111 are incorporated herein by reference.

What is claimed is:

1. An organotypic culture comprising an artificial stroma comprising a mixture of collagen and human fibroblasts isolated from a human colon or intestine, said stroma overlayed with epithelial cells isolated from fetal human colon, wherein said culture contains a growth factor that binds the insulin growth factor-1 (IGF-1) receptor selected from insulin and IGF-1, a growth factor that binds the epidermal growth factor (EGF) receptor selected from EGF and tumor growth factor-alpha (TGF-alpha), and the growth factor leukemia inhibitory factor (LIF), which binds the LIF receptor.

2. The culture according to claim 1, wherein said collagen is selected from the group consisting of human collagen type I and bovine collagen type I.

3. The culture according to claim 1, wherein said fibroblasts are selected from the group consisting of adult human colon fibroblasts, fetal human colon fibroblasts, adult human small intestinal fibroblasts, fetal human small intestinal fibroblasts, and human fibroblast stem cells.

4. The culture according to claim 3, wherein said stem cells are isolated from human bone marrow.

5. The culture according to claim 1, further comprising human smooth muscle cells embedded into said collagen.

6. The culture according to claim 1, further comprising a layer of endothelial cells underlying said collagen and fibroblast mixture.

7. The culture according to claim 1, comprising at least one matrix protein selected from the group consisting of Laminin-1 and Laminin-2.

8. An organotypic culture comprising an artificial stroma comprising a mixture of collagen and human fibroblasts isolated from a human colon or intestine, said stroma overlayed with epithelial cells isolated from fetal human colon, wherein said culture contains a growth factor that binds the IGF-1 receptor selected from insulin and IGF-1, a growth factor that binds the EGF receptor selected from EGF and tumor growth factor-alpha (TGF-alpha), the growth factor LIF, which binds the LIF receptor, the growth factor endothelin-3 (ET-3), which binds the ET-3 receptor, a growth factor that binds the hepatocyte growth factor (HGF) receptor selected from HGF and tumor growth factor-beta (TGF-beta), the growth factor stem cell factor (SCF), which binds the SCF receptor, and the growth factor autocrine motility factor (AMF), which binds the AMF receptor.

9. The culture according to claim 8, further comprising an additional component selected from the group consisting of transferrin, fetal calf serum, and combinations thereof.

10. A method of preparing an organotypic culture of claim 1 comprising:
   (a) assembling an artificial stroma by mixing collagen and fibroblasts;
   (b) seeding said artificial stroma with epithelial cells isolated from fetal human colon in the presence of a growth factor that binds the IGF-1 receptor selected from insulin and IGF-1, a growth factor that binds the EGF receptor selected from EGF and tumor growth factor-alpha (TGF-alpha), and the growth factor LIF, which binds the LIF receptor.

11. The method according to claim 10, wherein said collagen is selected from the group consisting of human collagen type I and bovine collagen type I.

12. The method according to claim 10, wherein said fibroblasts are selected from the group consisting of adult human colon fibroblasts, fetal human colon fibroblasts, adult human small intestinal fibroblasts, fetal human small intestinal fibroblasts, and human fibroblast stem cells.

13. The method according to claim 12, wherein said stein cells are isolated from human bone marrow.

14. The method according to claim 10, further comprising mixing human smooth muscle cells into said collagen mixture.

15. The method according to claim 10, further comprising layering said artificial stroma over a layer of endothelial cells.

16. The method according to claim 10, comprising introducing at least one matrix protein selected from the group consisting of Laminin-1 and Laminin-2 between said artificial stroma and said epithelial cells or overlaying said epithelial cells.

17. The method according to claim 10, wherein said culture further comprises one or more of a factor selected from the group consisting of endothelin-3, hepatocyte growth factor, stem cell factor and motility faetor.

18. The method according to claim 10, wherein said culture further comprises an additional component selected from the group consisting of transferrin, fetal calf serum and combinations thereof.

19. The method according to claim 10, further comprising seeding a malignant cell on the artificial stroma to create a model of tumor formation or tumor-stroma interaction.

* * * * *

UNITED STATES PATENT AND TRADEMARK OFFICE
CERTIFICATE OF CORRECTION

PATENT NO. : 7,217,570 B2  Page 1 of 1
APPLICATION NO. : 10/485283
DATED : May 15, 2007
INVENTOR(S) : Herlyn et al.

It is certified that error appears in the above-identified patent and that said Letters Patent is hereby corrected as shown below:

Col. 1, line 11, insert the following:

-- This invention was made with government support under National Institutes of Health Grant Nos. CA74294, PK50306, and CAI08185, awarded by the US Department of Health and Human Services. The government has certain rights in the invention. --

Signed and Sealed this

Sixteenth Day of September, 2008

JON W. DUDAS
*Director of the United States Patent and Trademark Office*